US011160224B2

(12) United States Patent
Beetham et al.

(10) Patent No.: US 11,160,224 B2
(45) Date of Patent: Nov. 2, 2021

(54) NON-TRANSGENIC HERBICIDE RESISTANT PLANTS

(71) Applicant: CIBUS US LLC, San Diego, CA (US)

(72) Inventors: Peter R. Beetham, Carlsbad, CA (US); Patricia L. Avissar, East Brunswick, NJ (US); Keith A. Walker, San Diego, CA (US); Richard A. Metz, Lawrenceville, NJ (US)

(73) Assignee: CIBUS US LLC, San Diego, CA (US)

( * ) Notice: Subject to any disclaimer, the term of this patent is extended or adjusted under 35 U.S.C. 154(b) by 1 day.

(21) Appl. No.: 16/049,561

(22) Filed: Jul. 30, 2018

(65) Prior Publication Data

US 2018/0355327 A1 Dec. 13, 2018

Related U.S. Application Data

(63) Continuation of application No. 11/941,666, filed on Nov. 16, 2007, now Pat. No. 10,035,991, which is a continuation of application No. 11/051,955, filed on Feb. 4, 2005, now abandoned, which is a continuation of application No. 09/685,403, filed on Oct. 10, 2000, now Pat. No. 6,870,075.

(60) Provisional application No. 60/173,564, filed on Dec. 30, 1999, provisional application No. 60/158,027, filed on Oct. 7, 1999.

(51) Int. Cl.
| | |
|---|---|
| *C12N 15/82* | (2006.01) |
| *A01H 1/00* | (2006.01) |
| *A01H 1/06* | (2006.01) |
| *A01H 5/10* | (2018.01) |
| *C12N 9/10* | (2006.01) |

(52) U.S. Cl.
CPC ............ *A01H 1/1235* (2021.01); *A01H 1/06* (2013.01); *A01H 5/10* (2013.01); *C12N 9/1092* (2013.01); *C12N 15/8213* (2013.01); *C12N 15/8275* (2013.01)

(58) Field of Classification Search
CPC ................................................ C12N 15/8274
See application file for complete search history.

(56) References Cited

U.S. PATENT DOCUMENTS

| | | |
|---|---|---|
| 4,545,060 A | 10/1985 | Arnon |
| 4,940,835 A | 7/1990 | Shah et al. |
| 4,945,050 A | 7/1990 | Sanford et al. |
| 5,100,792 A | 3/1992 | Sanford et al. |
| 5,145,783 A | 9/1992 | Kishore et al. |
| 5,204,253 A | 4/1993 | Sanford et al. |
| 5,302,523 A | 4/1994 | Coffee et al. |
| 5,310,667 A | 5/1994 | Eichholtz et al. |
| 5,312,910 A | 5/1994 | Kishore et al. |
| 5,334,711 A | 8/1994 | Sproat et al. |
| 5,565,350 A | 10/1996 | Kmiec |
| 5,627,061 A | 5/1997 | Barry et al. |
| 5,731,181 A | 3/1998 | Kmiec |
| 5,756,325 A | 5/1998 | Kmiec |
| 5,760,012 A | 6/1998 | Kmiec et al. |
| 5,780,296 A | 7/1998 | Holloman et al. |
| 5,795,972 A | 8/1998 | Kmiec |
| 5,804,425 A | 9/1998 | Barry et al. |
| 5,866,775 A | 2/1999 | Eichholtz et al. |
| 5,871,984 A | 2/1999 | Kmiec |
| 5,888,983 A | 3/1999 | Kmiec et al. |
| 5,945,339 A | 8/1999 | Holloman et al. |
| 6,004,804 A | 12/1999 | Kumar et al. |
| 6,010,907 A | 1/2000 | Kmiec et al. |
| 6,022,589 A | 2/2000 | Klosowski et al. |
| 6,066,786 A | 5/2000 | Rose-Fricker |
| 6,136,601 A | 10/2000 | Meyer, Jr. et al. |
| 6,174,694 B1 | 1/2001 | Havre et al. |
| 6,210,916 B1 | 4/2001 | Havre et al. |

(Continued)

FOREIGN PATENT DOCUMENTS

| | | |
|---|---|---|
| EP | 0293358 A2 | 11/1988 |
| EP | 0679657 A2 | 11/1995 |

(Continued)

OTHER PUBLICATIONS

GenBank Accession No. AAT45238.1 Heck et al (Year: 2016).*
GenBank Accession No. PHT41257.1 Kim et al (Year: 2017).*
Agarwal et al., Nucleotide replacement at two sites can be directed by modified single-stranded oligonucleotide in vitro and in vivo. Biomol Eng. Jan. 2003;20(1):7-20.
Alexeev and Yoon, Stable and inheritable changes in genotype and phenotype of albino melanocytes induced by an RNA•DNA oligonucleotide. Nat Biotechnol. Dec. 1998;16(13):1343-1346.
Baerson et al, Glyphosate-Resistant Goosegrass. Identification of a Mutation in the Target Enzyme 5-Enolpyruvylshikimate-3-Phosphate Synthase. Plant Physiol. Jul. 2002;129(3):1265-1275.
Beetham et al., 1999, A tool for functional plant genomics; Chimeric RNA/DNA olignucleotides cause in vivo gene-specific mutations. Proc Natl Acad Sci USA. Jul. 20, 1999;96(15):8774-8778.

(Continued)

*Primary Examiner* — David H Kruse

(74) *Attorney, Agent, or Firm* — Acuity Law Group, PC; Michael A. Whittaker

(57) ABSTRACT

The present invention relates to the production of a non-transgenic plant resistant or tolerant to a herbicide of the phosphonomethylglycine family, e.g., glyphosate. The present invention also relates to the use of a recombinagenic oligonucleobase to make a desired mutation in the chromosomal or episomal sequences of a plant in the gene encoding for 5-enol pyruvylshikimate-3-phosphate synthase (EPSPS). The mutated protein, which substantially maintains the catalytic activity of the wild-type protein, allows for increased resistance or tolerance of the plant to a herbicide of the phosphonomethylglycine family, and allows for the substantially normal growth or development of the plant, its organs, tissues or cells as compared to the wild-type plant irrespective of the presence or absence of the herbicide. The present invention also relates to a non-transgenic plant cell in which the EPSPS gene has been mutated, a non-transgenic plant regenerated therefrom, as well as a plant resulting from a cross using a regenerated non-transgenic plant having a mutated EPSPS gene.

10 Claims, 10 Drawing Sheets

Specification includes a Sequence Listing.

(56) References Cited

U.S. PATENT DOCUMENTS

| | | |
|---|---|---|
| 6,211,351 B1 | 4/2001 | Kumar et al. |
| 6,225,114 B1 | 5/2001 | Eichholtz et al. |
| 6,271,360 B1 | 8/2001 | Metz et al. |
| 6,410,226 B1 | 6/2002 | Kmiec et al. |
| 6,524,613 B1 | 2/2003 | Steer et al. |
| 6,573,046 B1 | 6/2003 | Kmiec et al. |
| 6,870,075 B1 | 3/2005 | Beetham et al. |
| 10,035,991 B2 | 7/2018 | Beetham et al. |

FOREIGN PATENT DOCUMENTS

| | | | |
|---|---|---|---|
| GB | 2326163 A | * | 12/1998 |
| JP | 64-039984 | | 2/1989 |
| WO | 9206201 A1 | | 4/1992 |
| WO | 9704103 A2 | | 2/1997 |
| WO | 9811214 A1 | | 3/1998 |
| WO | 9844140 A1 | | 10/1998 |
| WO | 9849350 A1 | | 11/1998 |
| WO | 9854330 A1 | | 12/1998 |
| WO | 9907865 A1 | | 2/1999 |
| WO | 9925853 A1 | | 5/1999 |
| WO | 9940789 A1 | | 8/1999 |
| WO | 9958702 A1 | | 11/1999 |
| WO | 9958723 A1 | | 11/1999 |
| WO | 0017329 A1 | | 3/2000 |
| WO | 0115740 A1 | | 3/2001 |
| WO | 2009002150 A1 | | 12/2008 |

OTHER PUBLICATIONS

Cole-Strauss et al., Correction of the mutations responsible for sickle cell anemia by an RNA•DNA oligonucleotide. Science. Sep. 6, 1996;273(5280):1386-1389.

Comai et al., An Altered aroA Gene Product Confers Resistance to the Herbicide Glyphosate. Science. Jul. 22, 1983;221(4608):370-371.

Communication pursuant to Article 94(3) EPC dated Apr. 15, 2008 in application EP 00970716.

Communication pursuant to Article 94(3) EPC dated Jun. 18, 2010 in EP application EP 09172695.

Communication pursuant to Article 96(2) EPC dated Apr. 20, 2007 in application EP 00970716.

Communication pursuant to Article 96(2) EPC dated Apr. 29, 2005 in application EP 00970716.

Communication pursuant to Article 96(2) EPC dated May 26, 2006 in application EP 00970716.

U.S. Office Action dated Feb. 13, 2002 in related U.S. Appl. 09/685,403.

Database EMBL [Online] EBI Hinxton; Oct. 22, 1992, Eichhotltz, et al, "Modified 5-enolpyruvyl-3-phosphoshikimate synthetase (2)" retrieved from EBI database accession No. AAR23062 abstract.

Database entry for 3-phosphoshikimate 1-carboxyvinyltransferase—Bacillus subtilis from website uniprot.org/uniprot/P20691 dated Oct. 5, 2011.

de Both, Selection of protoplasts for herbicide tolerance: different outcomes of the selection. Jan. 19, 2012:3pgs.

Dyer et al., Glyphosate Tolerance in Tobacco (*Nicotiana tabacum* L.). Plant Physiol. Nov. 1988;88(3):661-666.

Escorial et al., In vitro Culture Selection Increases Glyphosate Tolerance in Barley. Plant Cell Tissue and Organ Culture. 1996;46:179-186.

European Opposition documents cited in related European Patent No. 1223799, dated Jan. 27, 2012.

European Search Report for EPO Patent Application No. 09172695 dated Nov. 24, 2009.

Experimental result II Keygene, 3 pgs.

Final Rejection cited in related Japanese Patent Application No. 2001-527631, dated Jan. 10, 2012—Engl lang transl only.

Forlani et al., A glyphosate-resistant 5-enol-pyruvyl-shikimate-3-phosphate synthase confers tolerance to a maize cell line. Plant Science 1992;85(1):9-15.

Frame et al., Production of fertile transgenic maize plants by silicon carbide Whisker-mediated transformation. Plant J. 1994;6:941-948.

Funke et al., Structural Basis of Glyphosate Resistance Resulting from the Double Mutation Thr97 ->. Iie and Pro101 ->Ser in 5-Enolpyruvylshikimate-3-phosphate Synthase from *Escherichia coli*. J Biol Chem. (2009) 284:9854-9860.

Gallois et al., Electroporation of Tobacco Leaf Protoplasts Using Plasmid DNA or Total Genomic DNA. Methods Mol Biol. 1995;55:89-107.

Gamper et al., The DNA strand of chimeric RNA/DNA oligonucleotides can direct gene repair/conversion activity in mammalian and Plant cell-tree extracts. Nucleic Acids Res. Nov. 1, 2000;28(21):4332-4339.

Goldsbrough et al., Gene amplification in glyphosate tolerant tobacco cells. Plant Sci. 1990;72:53-62.

Gong et al., Characterization of 5-enolpyruvylshikimate 3-phosphate synthase gene from Camptotheca acuminate. Biologia Plantarum Jan. 2006;50(4):542-550.

Heck et al., 5-enolpyruvylshikimate-phosphate synthase. Gen Bank Accession AAT 45238.1, Jul. 1, 2004 (2 pages).

Hegele, et al., Simultaneous targeted exchange of two nucleotides by single stranded oligonucleotides clusters within a region of about fourteen nucleotides. BMC Mol Biol. Jan. 28, 2008;9:14 (11 pages).

Henner et al., The organization and Nucleotide Sequence of the Bacillus subtilis hisH, tyrA and aroE genes. Gene. 1986;49(1):147-152.

Hohn and Puchta, Gene therapy in plants. Proc Natl Acad Sci U S A. Jul. 20, 1999;96(15):8321-8323.

Kipp et al., Gene-Targeting in Plants via Site-Directed Mutagenesis. Methods Mol Biol. 2000;133:213-221.

Kishore and Shah, Amino Acid Biosynthesis Inhibitors as Herbicides. Annu Rev Biochem. 1988;57:627-663.

Kishore et al., Isolation, Purification and Characterization of a Glyphosate Tolerant Mutant *E. coli* EPSP Syntase. Fed Proc. 1986;45:1506 (abstract only).

Kochevenko and Willmitzer, Chimeric RNA/DNA Oligonucleotide-Based Site-Specific Modification of the Tobacco Acetelactate Syntase Gene. Plant Physiol. May 2003;132(1):174-184.

Kren et al., Targeted Nucleotide Exchange in the Alkaline PhosphataseGene of HuH-7 Cells Mediated by a ChimericRNA/DNA Oligonucleotide. Hepatology. Jun. 1997;25(6):1462-1468.

Majumder et al., Background-minimized Cassette Mutagenesis by PCR Using Cassette-specific Selection Markers: A Useful General Approach for Studying Structure-Function Relationships of Multisubstrate Enzymes. PCR Methods Appl. Feb. 1995;4(4):212-218.

Meredith, On Being Selective: Mutants from Cultured Cells. Plant Molecular Biol. Reporter, 1983;1(3):105-110.

Monsanto Company, Roundup PRO Concentrate Herbicide Safety Data Sheet, Jun. 29, 2011:9 pages.

Neve et al., Multiple herbicide resistance in a glyphosate-resistant rigid ryegrass (*Lolium rigidum*) population. Weed Sci. Nov. 1, 2004;52(6): 920-928, abstract only.

Ng et al, Gene polymorphisms in glyphosate-resistant and -susceptible biotypes of Eleusine indica from Malaysia. Weed Res. Apr. 2003;43(2):108-115.

Ng et al, Inheritance of glyphosate resistance in goosegrass (*Eleusine indica*). Weed Sci. 2004;52:564-570.

Notice of Opposition to European Patent Application EP 00970716 dated Sep. 9, 2010.

Oh and May, Oligonucleotide-directed plant gene targeting. Curr Opin Biotechnol. Apr. 2001;12(2):169-172.

Okuzaki and Toriyama, Chimeric RNA/DNA oligonucleotide-directed gene targeting in rice. Plant Cell Rep. Feb. 2004;22(7):509-512.

Padgette et al., Herbicide-Resistant Crops. CRC Lewis publishers, Duke Ed., 1996;Chap. 4: 53-84 and 4 pgs. of pictures.

Padgette et al., Site-directed Mutagenesis of a Conserved Region of the 5-Encolypyruvylshikimate-3-phosphate Synthase Active Site. J Biol Chem. Nov. 25, 1991;266(33):22364-22369.

Paszkowski et al., Gene targeting in plants. EMBO J. Dec. 20, 1988;7(13):4021-4026.

(56) References Cited

OTHER PUBLICATIONS

Powles and Preston, Evolved Glyphosate Resistance in Plants: Biochemical and Genetic Basis of Resistance. Weed Technol. 2006;20:282-289.
Putcha and Horn, From centriMorgans to base pairs: homologous recombination in plants. Trends Plant Sci. Oct. 1996;1(10):340-348.
Rice et al., Genetic Repair of Mutations in Plant Cell-free Extracts Directed by Specific Chimeric Oligonucleotides. Plant Physiol. Jun. 2000;123(2):427-438.
Rice, et al., The potential of nucleic acid repair in functional genomics. Nat Biotechnol. Apr. 2001;19(4):321-326.
Ruiter, et al., Spontaneous mutation frequency in plants obscures the effect of chimeraplasty, Plant Mol Biol. Nov. 2003;53(5):675-689.
Schaefer and Zyrd, Efficient gene targeting in the moss Physcomitrella patens,• Plant J. Jun. 1997;11(6):1195-1206.
Schultz et al., Insensitivity of 5-Enolpyruvylshikimic Acid-3-Phosphate Synthase to Glyphosphate Confers Resistance to this Herbicide in a Strain of Aerobacter aerogenes. Arch Microbiol. 1984;137:121-123.
Selvapandiyan, et al., Point mutation of a conserved arginine (104) to lysine introduces hypersensitivity to inhibition by glyphosate in the 5-enolpyruvylshikimate-3-phosphate synthase of Bacillus subtilis. FEBS Lett. Oct. 30, 1995;374(2):253-256.
Shah et at., Engineering Herbicide Tolerance in Transgenic Plants. Science. Jul. 25, 1986;233(4762):478-481.
Shuttleworth et al., Site-Directed Mutagenesis of Putative Active Site Residues of 5-Enolpyruvylshikimate-3-phosphate Synthase. Biochemistry. Jan. 5, 1999;38(1):296-302.
Shyr et al., Glyphosate selected amplification of the 5-enolypyruvylshikimate-3-phosphate synthase gene in cultured carrot cells. Mol Gen Genet. Apr. 1992;232(3):377-382.
Singer and McDaniel, Selection of Glyphosate-Tolerant Tobacco Calli and the Expression of this Tolerance in Renegerated Plants. Plant Physiol. Jun. 1985;78(2):411-416.
Sost and Amrhein, Substitution of Gly-96 to Ala in the 5-Enolpyruvylshikimate 3-Phosphate Synthase of Klebsiella pneumoniae Results in a Greatly Reduced Affinity for the Herbicide Glyphosate. Arch Biochem Biophys. Nov. 1, 1990;282(2):433-436.
Sost et al., Characterization of a glyphosate-insensitive 5-enolpyruvylshikimic acid-3phosphate synthase. FEBS Lett. 1984;173:238-241.
Stalker, et al., A Single Amino Acid Substitution in the Enzyme 5-Enolpyruvylshikimate-3-phosphate Synthase Confers Resistance to the Herbicide Glyphosate. J Biol Chem. Apr. 25, 1985;260(8):4724-4728.
Stallings et al., Structure and topological symmetry of the glyphosate target 5-enol-pyruvylshikimate-3-phosphate synthase: A distinctive protein fold. Proc Natl Acad Sci U S A. Jun. 1, 1991;88(11):5046-5050.
Summons to Attend Oral Proceedings dated Sep. 23, 2011 in related EP Patent Application No. 09172695.
Supplementary European Search Report dated Oct. 1, 2004 in EP application 00970716.
Townsend et al., High-frequency modification of plant genes using engineered zinc-finger nucleases. Nature. May 21, 2009;459(7245):442-445.
Wakelin and Preston, A target-site mutation is present in a glyphosate-resistant Lolium rigidum population. Weed Res. 2006;46:432-440.
Widholm et al., Glyphosate selection of gene amplification in suspension cultures of 3 plant species. Physiol Plant. Aug. 2001;112(4):540-545.
Yu et al, Glyphosate, paraquat and ACCase multiple herbicide resistance evolved in a Lolium rigidum biotype. Planta. Jan. 2007;225(2):499-513.
Zhang et al., Plant gene targeting and gene replacement: application to crop genetic improvement. Chin J Agr Biotechnol. 2008;5(2):93-99.
Zhu et al., Engineering herbicide-resistant maize using chimeric RNA/DNA oligonucleotides. Nat Biotechnol. May 2000;18(5):555-558.
Zhu et al., Targeted manipulation of maize genes in vivo using chimeric RNA/DNA oligonucleotides. Proc Natl Acad Sci U S A. Jul. 20, 1999;96(15):8768-8773.

\* cited by examiner

DNA sequence:
cccttcatgtcttttgtagaaaccccattatctttcttagggcccaattgaaaacccacattttctttcacctaaccca
ccaaagccttgcacatgttgacgtgaacaccaaactaacacgtgtcatactgccagtggttatgataaatgctcatacc
ataccagagtcatagagtttttggttggtgaaagatttgacggatgccttcttctcatttctcaccaactccctccaaa
cccaacaaaatgcttatattagcaaagccgccaaagtgtaaacgaaagtttataaatttcatttctgtgatcttacgta
attggaggaagatcaaaattttcaatccccattcttcgattgcttcaattgaagttttctccg

[transit peptide start]
ATGGCGCAAGTTAGCAGAATCTGCAATGGTGTGCAGAACCCATCTCTTATCTCCAATCTCTCGAAATCCAGTCAACGCA
AATCTCCCTTATCGGTTTCTCTGAAGACGCAGCAGCATCCACGAGCTTATCCGATTTCGTCGTCGTGGGGATTGAAGAA
GAGTGGGATGACGTTAATTGGCTCTGAGCTTCGTCCTCTTAAGGTCATGTCTTCTGTTTCACGGCGGAG

[mature peptide starts]
AAAGCGTCGGAGATTGTACTTCAACCCATTAGAGAAATCTCCGGTCTTATTAAGCTTCCTGGCTCCAAGTCTCTATCAA
ATCGGATCCTGCTTCTCGCTGCTCTGTCTGAGGTATATATCACTTCGTTTCGTCCTTCTCTGTAATCTGAACTTAGATT
ATAAAGATTGATACTTTACCATTTTGCTGTGGTTTTATAGGGAACAACTGTAGTGGACAACTTGTTGAATAGCGATGAC
ATCAATTACATGCTTGATGCGTTGAAGAGATTGGGACTTAATGTGGAAACTGACAGTGAAAATAATCGTGCTGTAGTTG
AAGGATGTGGCGGGATATTCCCAGCTTCCATAGATTCAAAGAGTGATATCGAACTTTACCTCGGTAATGCAGGAACAGC
AATGCGTCCACTTACCGCTGCGGTCACTGCTGCAGGTGGAAACGCAAGGTAGATTGAAGGAGTTGATGCTTCTTGGTAT
TTGATGTTTAAGGAATGGAGCTTTTGTTGATGCTTATGATCCATTTATTCCAGTTATGTGCTTGATGGGGTGCCTCGT
ATGAGAGAAAGACCTATAGGGGATTTGGTTGTTGGTCTTAAGCAGCTTGGTGCTGATGTTGAATGTACTCTTGGAACTA
ACTGCCCTCCTGTTCGTGTCAACGCTAATGGTGGCCTTCCCGGTGGAAAGGTTAGATCTTGCAAATGGCATGTGAATAT
GTAATCTCGTTCCTTACTCTATGAACACTTGCAGAAATGTGTGTTCATCATAGCCTTAGCTTGACAAGATTTCAGTTTT
TAATCTACTCTCAACGGATGGATCCTAAAATAGAATCGGATTTGGTGATTGGTTTTCGTTCTCGATTACCGTTTTCGTT
GTATGATTTCTTGATTAACAATTAGGAGACATGTTATGCATTTGCAGGTGAAGCTTTCTGGATCAATTAGTAGTCAGTA
CTTGACTGCTCTGCTCATGTCTGCTCCCTTAGCTCTTGGAGACGTCGAGATTGAGATTGTCGATAAATTAATTTCTGTT
CCATATGTTGAAATGACATTGAAGTTGATGGAACGTTTCGGGGTTAGTGTCGAGCATAGTGATAGCTGGGATCGTTTCT
TTGTCAAGGGCGGGCAAAAATACAAGTAGGAGTTATTCTTTTCTTCCTTTTCTGAAATCACATCCCTTAGCTTGACAAT
ATAATGACTAAAAGGTGAATGATTCAGGTCTCCGGGTAATGCGTATGTAGAAGGTGATGCTTCTAGTGCATGTTATTTC
TTGGCTGGTGCTGCCATTACCGGTGAAACTGTCACAGTCGAAGGTTGTGGAACTACCAGCTTGCAGGTAATATTTGTAC
ACTGAATCATCGACGAGGCTGTTAAGTTTATAGTGAAATTCGTCTAGGTCAAAGTTTCATCTTTTGACAAGTTGTATAT
AACATATTCGCAAGATTCTAAGCTCAATTTTTGTGATGAATCTCTAGGGAGATGTAAAATTCGCCGAGGTCCTTGAGAA
AATGGGATGTAAAGTGTCCTGGACAGAGAACAGTGTGACTGTGACAGGACCACCTAGAGATGCTTTTGGAATGAGACAC
TTGCGGGCTATTGATGTCAACATGAACAAAATGCCTGATGTAGCCATGACCCTTGCCGTCGTTGCTCTCTTTGCTGACG
GTCCAACCACCATTAGAGATGGTAAGTAAAAAGCTCTCTCTTATAATTAAGGTTTCTCAATATTCATGATCACTTAATT
CTGTTTGGTTAATATAGTGGCTAGCTGGAGAGTAAAGGAGACAGAAAGGATGATTCCATTTGCACAGAGCTTAGAAAA
GTAAGAGATTCTTATCTCTCTTTCTGTCTCTTGACAGTGCTCATTCTAAGTAATTAGCTCATAAATTTGTGTGTTTG
TGTTCAGCTGGGAGCTACAGTGGAAGAAGGTTCAGATTATTGTGTGATAACTCCGCCAAAAAGGTGAAAACGGCAGAG
ATTGATACATATGATGATCATAGAATGGCAATGGCATTCTCTCTTGCAGCTTGTGCTGATGTTCCAATCACCATCAACG
ACTCTGGTTGCACCAGGAAAACCTTCCCCGACTACTTCCAAGTACTTGAAAGAATCACAAAGCACTAAacaataaactc
tgtttttcttctgatccaagctt

Fig. 1A

Protein sequence:
MAQVSRICNGVQNPSLISNLSKSSQRKSPLSVSLKTQQHPRAYPISSSWGLKKSGMTLIGSELRPLKVMSSVSTAE
KASEIVLQPIREISGLIKLPGSKSLSNRILLAALSEGTTVVDNLLNSDDINYMLDALKRLGLNVETDSENNRAVV
EGCGGIFPASIDSKSDIELYLGNAGTAMRPLTAAVTAAGGNASYVLDGVPRMRERPIGDLVVGLKQLGADVECTLG
TNCPPVRVNANGGLPGGKVKLSGSISSQYLTALLMSAPLALGDVEIEIVDKLISVPYVEMTLKLMERFGVSVEHSD
SWDRFFVKGGQKYKSPGNAYVEGDASSACYFLAGAITGETVTVEGCGTTSLQGDVKFAEVLEKMGCKVSWTENSV
TVTGPPRDAFGMRHLRAIDVNMNKMPDVAMTLAVVALFADGPTTIRDVASWRVKETERMIAICTELRKLGATVEEG
SDYCVITPPKKVKTAEIDTYDDHRMAMAFSLAACADVPITINDSGCTRKTFPDYFQVLERITKH

Fig. 1B

Arabidopsis thaliana wild type sequence:

| Position | 173 | 174 | 175 | 176 | 177 | 178 | 179 | 180 | 181 | 182 | 183 |
|---|---|---|---|---|---|---|---|---|---|---|---|
| | L | G | N | A | G | T | A | M | R | P | L |
| | CTC | GGT | AAT | GCA | GGA | ACA | GCA | ATG | CGT | CCA | CTT |

Arabidopsis thaliana mutant sequences:

| Name | | | | | | | | | | | |
|---|---|---|---|---|---|---|---|---|---|---|---|
| $A_{177}$ | CTC | GGT | AAT | GCA | GCA | ACA | GCA | ATG | CGT | CCA | CTT |
| | L | G | N | A | A | T | A | M | R | P | L |
| $I_{178}$ | CTC | GGT | AAT | GCA | GGA | ATA | GCA | ATG | CGT | CCA | CTT |
| | L | G | N | A | G | I | A | M | R | P | L |
| $A_{177}I_{178}$ | CTC | GGT | AAT | GCA | GCA | ATA | GCA | ATG | CGT | CCA | CTT |
| | L | G | N | A | A | I | A | M | R | P | L |
| $I_{178}S_{182}$ | CTC | GGT | AAT | GCA | GGA | ATA | GCA | ATG | CGT | TCA | CTT |
| | L | G | N | A | G | I | A | M | R | S | L |
| $A_{177}S_{182}$ | CTC | GGT | AAT | GCA | GCA | ACA | GCA | ATG | CGT | TCA | CTT |
| | L | G | N | A | A | T | A | M | R | S | L |
| $A_{177}I_{178}S_{182}$ | CTC | GGT | AAT | GCA | GCA | ATA | GCA | ATG | CGT | TCA | CTT |
| | L | G | N | A | A | I | A | M | R | S | L |
| $V_{178}S_{182}$ | CTC | GGT | AAT | GCA | GGA | GTA | GCA | ATG | CGT | TCA | CTT |
| | L | G | N | A | G | V | A | M | R | S | L |
| $L_{178}S_{182}$ | CTC | GGT | AAT | GCA | GGA | TTA | GCA | ATG | CGT | TCA | CTT |
| | L | G | N | A | G | L | A | M | R | S | L |
| $A_{177}V_{178}$ | CTC | GGT | AAT | GCA | GCA | GTA | GCA | ATG | CGT | CCA | CTT |
| | L | G | N | A | A | V | A | M | R | P | L |
| $A_{177}L_{178}$ | CTC | GGT | AAT | GCA | GCA | TTA | GCA | ATG | CGT | CCA | CTT |
| | L | G | N | A | A | L | A | M | R | P | L |

Fig. 2

```
                    1                                                                                             100
atepspscDNA.seq  (1) ATGGCGCAAGTTAGCAGAATCTGCAATGGTGTGCAGAACCAT---CTCTTATCTCCAATTCTCTGAAATCCAGTCACGCAAATCTCC---CTTATCGG
bnepscdna.seq    (1) ATGGCGCAATCTAGCAGAGAATCTGCCATGGCGTGCAGAACCCATGTGTTATCATCTCCAATCTCTCCAATTCTCCAACCAAAACAAATCACC---TTTCTCCG
petaroacdna.seq  (1) ATGGCACAAATTAACAACATGGCTCTCAAGGATACAAAACCCTTA---ATCCCAATTCCAATTTCCATAAACCCCAAGTTCCTAAATCTTCAAGTTTTCTTG
zmepsps.seq      (1) GCGG---------------------------------------------------------------------------------------------

101                                                                                             200
atepspscDNA.seq  (95) TTTTCT---CTGAAGACGCAGCAGCATCCACGAGCTTATCCGATTTCGTCGTCGTGGGGATTGAAGAAGAGAGTGGGATGACGTTATTGGCTCTGAGCTTCG
bnepscdna.seq    (98) TCTCC----TTGAAGACGCCATCAGC---CTCGAGCTT---------CTTCGTCGGGATTGAAGAAGAGAGTGAACGATGCTAAACGGTTCTGTAATTCG
petaroacdna.seq  (98) TTTTTGGATCTAAAAAACTGAAAAAATTCAGCAGATT----------CTATGTTGGTTTGTTGAAAAAAAGATTCAATTTT-----TATGCAAAAGTTTTG
zmepsps.seq       (5) -----------------------------------------------------------------------------------GTGCCGAGG-------

201                                                                                             300
atepspscDNA.seq (192) TCCTCTTAAGGTCATGTCTCTGTTTCCACGGGGAGAAAGCGTCGGAGATTGTACTTCAACCCATTAGAGAAATCTCCGGTCTTATTAAGCTTCCTGGC
bnepscdna.seq   (180) CCCGGTTAAGGTAACAGCTTCTCGTTTCCACGTCCGAGAAAGCTTCAGAGATGTGCTTCAACAATCAGAGAAATCTCGGGTCTCATTAAGCTACCCGGA
petaroacdna.seq (180) TTCCTTTAGGATTTCAGCATCAGTGGCTACAGCACAGAGAAGCCTTCGCAACAGAAGATTTCAGGACCTGTTAAATGCCTGGC
zmepsps.seq      (14) --------------------AGATCGTGCTGCAGCCAGCCATCAAGGAGATCTCCGGCACCCTCAAGCTGCCGGGG 301                                                                                             400
atepspscDNA.seq (292) TCCAAGTCTCTATCAAATCGGATCCTGCTTCTCGCTGCTCTGAGGGAACACTGTTGGACAACTTGTGAATAGCGATGACATCAATTACATGC
bnepscdna.seq   (280) TCCAAATCTCTCCAATCGGATCCGATCCTCTTGCCGTCTTATCGAGGGAACACTGTTGGACAACTTGTGACAGTGATGATGACATCAATTACATGC
petaroacdna.seq (280) TCTAAATCATTATCTAAATAGAATTCCCTTTCTGCCTTATCTGAAGGAACAACTGGTTGACAATTTACTAAGTAGTGATGATGATCATTACATGC
zmepsps.seq      (67) TCCAAGTCGCTTTCCAACCGGATCTCCGGATCCTCCGTCCGAGCAGTTGATAACCTGCTGAACAGTGGTTGATAACCTGCTGAACAGTGGATGCTCCACTACATGC 401                                                                                             500
atepspscDNA.seq (392) TTGATGCGTTGAAGAGATTGGGACTTAAATGCAAGACTTGAACAGTGAAAATAATCGTGCTGTAGTTGAAGGATGTGGCGGGATATTCCCAGCTTCCATAGA
bnepscdna.seq   (380) TTGATGCGTTGAAGAGCTCGGGCTTAACGTGGACTGACAGTGTAAACAACCGTGCGGTTGTTGAAGGATGCGGTGGAATATTCCCAGCTTCCTTAGA
petaroacdna.seq (380) TTGGTGCCTTGAAAACACTTGGACTTGATCTAGAAGAAGATAGTGCAAACCAACGAGCTGTTGTTGAAGGTTGGGCTTTCCCGTTGGTAAAGA
zmepsps.seq     (167) TCGGGGCCTTGAAGGACTCTTGGTCTCTGTCGAAGCGGACAAAGCTGCCAAAAGAGCTGTTCTGTAGTTGTTGGCGTGTGGTGGAAGTTCCCAGTTG---AGGA 501                                                                                             600
atepspscDNA.seq (492) TTCAAAGAGTGATATCGAACTTACCTGCGTAATGCAAGAACAGCAATGCTCCACTTACCGTCGGTCACTGCTGCAGGTGGAACGCAAGTTATGTG
bnepscdna.seq   (480) TTCCAAGAGTGATATTGAGTGTACCTTGGAATGCAGGAACAGCAGGAACAGCCATGCGTCCACTCACCGCCGGTCAGTTACAGCTGCAGGTGGCACGCGAGTTATGTA
petaroacdna.seq (480) GTCCAAGGAAGAAGAATTCAACTGTTCCTTGGGAATGCAGGAACAGCAGGAACAGCAGGAACAGCAGGAACTGGGCAGTACTACAGCAGCAGCACAGCAGCGAATTCAAGGTATGTA
zmepsps.seq     (264) TGCTAAAGAGGAAGTGCAGCTCTTCTTGGGGAATGCTGGAATGCTGGAACTGGAATGCTGGAACTGGAATGCTGGAACTGGAACTGTTACTGCTGCTGTCGTCGTGGTGGAAATGCAACTTACGTG
```

```
                    1201                                                                                           1300
atepspsDNA.seq (1192) ATTGATGTCAACATGAACATGAACAAAATGCCCTGATGTAGCCATGACCCTGCGTCGTTGCTCTCTTTGCTGACGGTCCAACCACCATTAGAGATGTGGCTAGCT
bnepscdna.seq  (1180) GTTGATGTCAACATGAACATGAACAAAATGCCCTGATGTAGCCATGACTCTAGACCGTTGTTGCTGCCGATGGTCCAACCACCATCAGAGATGTGGCTAGCT
petaroacdna.seq(1180) ATTGATGTGAACATGAATAAAATGCCTGATGTTGCCATGACACTTGCTGTTGTTGTTGCACTTTATGCTGATGGTCCACAGCTATAAGAGATGTTGCTAGCT
zmepsps.seq    (964)  ATTGATGTCAACATGAACAAGATGCCTGATGTCGCCATGACCCTTGCTGTGTGGTTGCCCTCTTGCCGATGGCCATCAGACATCAGAGACGTGGCTTCCT
                    1301                                                                                           1400
atepspsDNA.seq (1292) GGAGAGTAAGGAGACAGAGAAGGATGATTGCCATTTGCACAGAGCTTAGAAAACTGGGAGCTACAGTGGAAGAAGGTTCAGATTATTGTGATAACTCC
bnepscdna.seq  (1280) GGAGAGTTAAGGAGACAGAGAGGATGATTGCCATTTGCACAGAGCTTAGACAGTCCTTGGAGCTACAGTGGAAGAAGGTTCAGATTATTGTGATAACTCC
petaroacdna.seq(1280) GGAGAGTCAAGGAAACTGAGCGCCATGATCGCCATATGCCATCGCCATTGCCATAATGCCATATGCAGAACTTAGGAAGTTAGGAGCAACCGTTGAAGAAGGACCAGACTACTGCATAATCACCCC
zmepsps.seq    (1064) GGAGAGTAAAGGAGACACCGGAGGATGGTTGCGATCCGGAGCCGAGCATCTGGGGGCACCATCTGGGAAGGTCGGGACTACTGCATCATCACGCC
                    1401                                                                                           1500
atepspsDNA.seq (1392) GCCCAAAAAGGTGAAAACGGCAGAGATTGATACATATGATGATGATCATAGAATGGCAATGGCATTCTCTTGCAGCTTGTGCTGATGTTCCAATCACCATC
bnepscdna.seq  (1380) ACCAGCAAAGGTGAAACGTGGAAACCGGCGGAGATTGATACGTATGATGATCATAGAATGGCGATGGCGTTCTCGCTTGCCTTGCAGCTTGTGCTGATGTTCAGTCACCATC
petaroacdna.seq(1380) ACCGGAGAAACTAAATGTGACCGATATTGATACAGATGATCACAGGATGGCATTGGCCATGGCTTTTTCTTTCGCTTGCTTGTGCAGATGTTCCCGTCACCATC
zmepsps.seq    (1164) GCCGGAGAAGCTGAACGTGACCGATCGACGACGTAGCCAGGATGGCGATGGCCATGGCCTTCCTGCCCCGTGTGCCGAGGTCCCCGGTCACCATC
                    1501                                                                                           1572
atepspsDNA.seq (1492) AACGACTCTGGTTGCACCAGGAAACCTTCCCGACTACTTCCAAGTACTTGAAAGAATCACAAGCACTAA
bnepscdna.seq  (1480) AAGGATCCTGGCTGCACCAGGAAGACTTTCCCTGACTACTTCCAAGTCCTTGAAAGTATCACAAAGCATTAA
petaroacdna.seq(1480) AATGACCCTGGCTGCACGCGGAAAACCTTCCTAACTACTTTGATGTACTTCAGCAGTACTTCCAAGCATTGA
zmepsps.seq    (1264) CGGGACCCTGGGTGCACCGGAAGACCTTTCCCGACTACTTCGATGTCGAGCACTTTCGTCAAGAATTAA
```

Fig. 3C

```
                      1                                                                                                  100
atepsps.PRO    (1)    MAQVSRICNGVQNP-SLISNLSKSSQRKSPLSVSLKTQQHPRAYPISSWGLKKSGMTLIGSELR-----PLKVMSSVSTAEKASEIVLQPIREISGLI
bnepsps.PRO    (1)    MAQSSRICHGVQNFCVIISNLSKSNQNKSPFSVSLKTHQ-----PRASSWGLKKSGTMLNGSVIR------PVKVTASVSTSEKASEIVLQPIREISGLI
petaroa.PRO    (1)    MAQINNMAQGIQTL-NPNSNFHKPQVPKSSSSFLVFGSKK-----LKNSA-----NSMLVLKEDSIFMQKFCSFRISASVATAQKPSEIVLQPIKEISGTV
zmepsps.PRO    (1)    AG--------------------------------------------------------------------AEEIVLQPIKEISGTV 101                                                                                                200
atepsps.PRO    (94)   KLPGSKSLSNRILLLAALSEGTTVVDNLLNSDDINYMLDALKRLGLNVETDSENNRAVVEGCGGIFPASIDSKSDIELYLGNAGTAMRPLTAAVTAAGGN
bnepsps.PRO    (90)   KLPGSKSLSNPILLLAALSEGTTVVDNLLNSDDINYMLDALKKLGLNVERDSVNNRAVVEGCGGIFPASLDSKSDIELYLGNAGTAMRPLTAAVTAAGGN
petaroa.PRO    (90)   KLPGSKSLSNRILLLAALSEGTTVVDNLLSSDDIHYMLGALKTLGLHVEEDSANQRAVVEGCGLFPVGKESKEEIQLFLGNAGTAMRPLTAAVTVAGGN
zmepsps.PRO    (19)   KLPGSKSLSNRILLLAALSEGTTVVDNLLNSEDVHYMLGALRTLGLSVEADKAAKRAVVVGCGGKFPV-EDAKEEVQLFLGNAGTAMRPLTAAVTAAGGN 201                                                                                                300
atepsps.PRO    (194)  ASYVLDGVPRMRERPIGDLVVGLKQLGADVECTLGTNCFPVRVNANGGLPGGKVKLSGSISSQYLTALLMSAPLALGDVEIEIVDKLISVPYVEMTLKLM
bnepsps.PRO    (190)  ASYVLDGVPRMRERPIGDLVVGLKQLGADVECTLGTNCPPVRVNANGGLPGGKVKLSGSISSQYLTALLMAAPLALGDVEIEIIDKLISVPYVEMTLKLM
petaroa.PRO    (190)  SRYVLDGVPRMRERPISDLVDGLKQLGAEVDCFLGTKCPPVRIVSKGGLPGGKVKLSGGISSQYLTALLMAAPLALGDVEIEIIDKLLSVPYVEMTLKLM
zmepsps.PRO    (118)  ATYVLDGVPRMRERPIGDLVVGLKQLGADVDCFLGTDCFPVRVNGIGGLPGGKVKLSGSISSQYLSALLMAAPLALGDVEIEIIDKLISIPYVEMTLRLM 301                                                                                                400
atepsps.PRO    (294)  ERFGVSVEHSDSWDRFFVKGGQKYKSPGNAYVEGDASSACYFLAGAAITGETVIVEGCGTTSLQGDVKFAEVLEKMGCKVSWTENSVTVTGPPRDAFGMR
bnepsps.PRO    (290)  ERFGVSAEHSDSWDRFFVKGGQKYKSPGNAYVEGDASSASYFLAGAAITGETVTVEGCGTTSLQGDVKFAEVLEKMGCKVSWTENSVTVTGPSRDAFGMR
petaroa.PRO    (290)  ERFGISVEHSSSWDRFFVRGGQKYKSPGKAFVEGDASSASYFLAGAAVTGGTITVEGCGTITVEGCGTNSLQGDVKFAEVLEKMGAEVTWTENSVTVTVKGPPRSSSGRK
zmepsps.PRO    (218)  ERFGVKAEHSDSWDRFYIKGGQKYKSPKNAVFEGDASSASYFLAGAAITGGTVTVEGCGTTSLQGDVKFAEVLEMMGAKVTWTETSVTVTGPPREPFGRK 401                                                                                                500
atepsps.PRO    (394)  HLRAIDVRMNKMPDVAMTLAVVALFADGPTTIRDVASWRVKETERMIAICTELRKLGATVEEGSDYCVIITPFKKVTAEIDTYDDHRMAMAFSLAACADV
bnepsps.PRO    (390)  HLRAVDVNMNKMPDVAMTLAVVALFADGPTTIRDVASWRVKETERMIAICTELRKLGATVEEGSDYCVIITPPAKVKPAEIDTYDDHRMAMAFSLAACADV
petaroa.PRO    (390)  HLRAIDVNMNKMPDVAMTLAVVALYADGPTAIRDVASWRVKETERMIAICTELRKLGATVEEGPDYCIITPPEKLNVTDIDTYDDHRMAMAFSLAACADV
zmepsps.PRO    (318)  HLKAIDVNMNKMPDVAMTLAVVALFADGPTAIRTELTKLGASVEEGPDYCIITPPEKLNVTAIDTYDDHRMAMAFSLAACAEV 501                527
atepsps.PRO    (494)  PITINDSGCTRKTFPDYFQVLERITKH
bnepsps.PRO    (490)  PVTIKDPGCTRKTFPDYFQVLESITKH
petaroa.PRO    (490)  PVTINDPGCTRKTFPNYFDVLQQYSKH
zmepsps.PRO    (418)  PVTIRDPGCTRKTFPDYFDVLSTFVKN
```

Fig. 4

Oligo Name    Oligo Sequence (5'→3')

ATEPS-A177
    CGTTTCCACCTGCAGCAGTGACCGCAGCGGTAAGTGGACGCATTGCTGTTGCTGCATTACCGAG

ATEPS-AI
    CGTTTCCACCTGCAGCAGTGACCGCAGCGGTAAGTGGACGCATTGCTATTGCTGCATTACCGAG

ATEPS-IS
    CGTTTCCACCTGCAGCAGTGACCGCAGCGGTAAGTGAACGCATTGCTATTGCTGCATTACCGAG

ATEPS-AS
    CGTTTCCACCTGCAGCAGTGACCGCAGCGGTAAGTGAACGCATTGCTGTTGCTGCATTACCGAG

ATEPS-AIS
    CGTTTCCACCTGCAGCAGTGACCGCAGCGGTAAGTGAACGCATTGCTATTGCTGCATTACCGAG

ATEPS-I177
    CGTTTCCACCTGCAGCAGTGACCGCAGCGGTAAGTGGACGCATTGCTGTTATTGCATTACCGAG

ATEPS-VS
    CGTTTCCACCTGCAGCAGTGACCGCAGCGGTAAGTGAACGCATTGCTACTCCTGCATTACCGAG

ATEPS-LS
    CGTTTCCACCTGCAGCAGTGACCGCAGCGGTAAGTGAACGCATTGCTAATCCTGCATTACCGAG

ATEPS-AV
    CGTTTCCACCTGCAGCAGTGACCGCAGCGGTAAGTGGACGCATTGCTACTGCTGCATTACCGAG

ATEPS-AL
    CGTTTCCACCTGCAGCAGTGACCGCAGCGGTAAGTGGACGCATTGCTAATGCTGCATTACCGAG

FIG. 5

NON-TRANSGENIC HERBICIDE RESISTANT PLANTS

The present application is a continuation of U.S. patent application Ser. No. 11/941,666, filed Nov. 16, 2007, issued as U.S. Pat. No. 10,035,991 on Jul. 31, 2018, which is a continuation of U.S. patent application Ser. No. 11/051,955, filed Feb. 4, 2005 which is a continuation of U.S. patent application Ser. No. 09/685,403, filed Oct. 10, 2000, now U.S. Pat. No. 6,870,075, which claims priority to U.S. Provisional Application No. 60/158,027, filed Oct. 7, 1999 and to U.S. Provisional Application No. 60/173,564, filed Dec. 30, 1999, the disclosures of each of which are incorporated by reference herein in their entirety.

1. FIELD OF THE INVENTION

The present invention relates to the production of a non-transgenic plant resistant or tolerant to a herbicide of the phosphonomethylglycine family, e.g., glyphosate. The present invention also relates to the use of a recombinagenic oligonucleobase to make a desired mutation in the chromosomal or episomal sequences of a plant in the gene encoding for 5-enol pyruvylshikimate-3-phosphate synthase (EPSPS). The mutated protein, which substantially maintains the catalytic activity of the wild-type protein, allows for increased resistance or tolerance of the plant to a herbicide of the phosphonomethylglycine family, and allows for the substantially normal growth or development of the plant, its organs, tissues or cells as compared to the wild-type plant irrespective of the presence or absence of the herbicide. The present invention also relates to a non-transgenic plant cell in which the EPSPS gene has been mutated, a non-transgenic plant regenerated therefrom, as well as a plant resulting from a cross using a regenerated non-transgenic plant having a mutated EPSPS gene.

2. BACKGROUND TO THE INVENTION

2.1 Phosphonomethylglycine Herbicides

Herbicide-tolerant plants may reduce the need for tillage to control weeds thereby effectively reducing soil erosion. One herbicide which is the subject of much investigation in this regard is N-phosphonomethylglycine, commonly referred to as glyphosate. Glyphosate inhibits the shikimic acid pathway which leads to the biosynthesis of aromatic compounds including amino acids, hormones and vitamins. Specifically, glyphosate curbs the conversion of phosphoenolpyruvic acid (PEP) and 3-phosphoshikimic acid to 5-enolpyruvyl-3-phosphoshikimic acid by inhibiting the enzyme 5-enolpvruvylshikimate-3-phosphate synthase (hereinafter referred to as EPSP synthase or EPSPS). For purposes of the present invention, the term "glyphosate" includes any herbicidally effective form of N-phosphonomethylglycine (including any salt thereof), other forms which result in the production of the glyphosate anion in plants and any other herbicides of the phosphonomethylglycine family.

Tolerance of plants to glyphosate can be increased by introducing a mutant EPSPS gene having an alteration in the EPSPS amino acid coding sequence into the genome of the plant. Examples of some of the mutations in the EPSPS gene for inducing glyphosate tolerance are described in the following patents: U.S. Pat. Nos. 5,310,667; 5,866,775; 5,312,910; 5,145,783. These proposed mutations typically have a higher $K_i$ for glyphosate than the wild-type EPSPS enzyme which confers the glyphosate-tolerant phenotype, but these variants are also characterized by a high $K_m$ for PEP which makes the enzyme kinetically less efficient (Kishore et al., 1988, Ann. Rev. Biochem. 57:627-663; Schulz et al., 1984, Arch. Microbiol. 137: 121-123; Sost et al., 1984, FEBS Lett. 173: 238-241; Kishore et al., 1986, Fed. Proc. 45: 1506; Sost and Amrhein, 1990, Arch. Biochem. Biophys. 282: 433-436). Many mutations of the EPSPS gene are chosen so as to produce an EPSPS enzyme that is resistant to herbicides, but unfortunately, the EPSPS enzyme produced by the mutated EPSPS gene has a significantly lower enzymatic activity than the wild-type EPSPS. For example, the apparent $K_m$ for PEP and the apparent $K_i$ for glyphosate for the wild-type EPSPS from *E. coli* are 10 µM and 0.5 µM, while for a glyphosate-tolerant isolate having a single amino acid substitution of alanine for glycine at position 96, these values are 220 µM and 4.0 mM, respectively. A number of glyphosate-tolerant EPSPS genes have been constructed by mutagenesis. Again, the glyphosate-tolerant EPSPS had lower catalytic efficiency ($V_{max}/K_m$), as shown by an increase in the $K_m$ for PEP, and a slight reduction of the $V_{max}$ of the wild-type plant enzyme (Kishore et al., 1988, Ann. Rev. Biochem. 57:627-663).

Since the kinetic constants of the variant enzymes are impaired with respect to PEP, it has been proposed that high levels of overproduction of the variant enzyme, 40-80 fold, would be required to maintain normal catalytic activity in plants in the presence of glyphosate (Kishore et al., 1988, Ann. Rev. Biochem. 57:627-663). It has been shown that glyphosate-tolerant plants can be produced by inserting into the genome of the plant the capacity to produce a higher level of EPSP synthase in the chloroplast of the cell (Shah et al., 1986, Science 233, 478-481), which enzyme is preferably glyphosate-tolerant (Kishore et al., 1988, Ann. Rev. Biochem. 57:627-663).

The introduction of the exogenous mutant EPSPS genes into plant is well documented. For example, according to U.S. Pat. No. 4,545,060. to increase a plant's resistance to glyphosate, a gene coding for an EPSPS variant having at least one mutation that renders the enzyme more resistant to its competitive inhibitor, i.e., glyphosate, is introduced into the plant genome. However, many complications and problems are associated with these examples. Many such mutations result in low expression of the mutated EPSPS gene product or result in an EPSPS gene product with significantly lower enzymatic activity as compared to wild type. The low expression or low enzymatic activity of the mutated enzyme results in abnormally low levels of growth and development of the plant.

While such variants in the EPSP synthases have proved useful in obtaining transgenic plants tolerant to glyphosate, it would be increasingly beneficial to obtain a variant EPSPS gene product that is highly glyphosate-tolerant but still kinetically efficient, such that improved tolerance can be obtained with a wild-type expression level.

2.2 Recombinagenic Oligonucleobases

Recombinagenic oligonucleobases and their use to effect genetic changes in eukaryotic cells are described in U.S. Pat. No. 5,565,350 to Kmiec (Kmiec I). Kmiec I teaches a method for introducing specific genetic alterations into a target gene. Kmiec I discloses, inter alia, recombinagenic oligonucleobases having two strands, in which a first strand contains two segments of at least 8 RNA-like nucleotides that are separated by a third segment of from 4 to about 50 DNA-like nucleotides, termed an "interposed DNA segment." The nucleotides of the first strand are base paired to DNA-like nucleotides of a second strand. The first and second strands are additionally linked by a segment of single stranded nucleotides so that the first and second strands are parts of a single oligonucleotide chain. Kmiec I further teaches a method for introducing specific genetic alterations into a target gene. According to Kmiec I, the sequences of the RNA segments are selected to be homologous, i.e., identical, to the sequence of a first and a second fragment of the target gene. The sequence of the interposed DNA segment is homologous with the sequence of the target gene between the first and second fragment except for a region of difference, termed the "heterologous region." The heterologous region can effect an insertion or deletion, or can contain one or more bases that are mismatched with the sequence of target gene so as to effect a substitution. According to Kmiec I, the sequence of the target gene is altered as directed by the heterologous region, such that the target gene becomes homologous with the sequence of the recombinagenic oligonucleobase. Kmiec I specifically teaches that ribose and 2'-O-methylribose, i.e., 2'-methoxyribose, containing nucleotides can be used in recombinagenic oligonucleobases and that naturally-occurring deoxyribose-containing nucleotides can be used as DNA-like nucleotides.

U.S. Pat. No. 5,731,181 to Kmiec (Kmiec II) specifically disclose the use of recombinagenic oligonucleobases to effect genetic changes in plant cells and discloses further examples of analogs and derivatives of RNA-like and DNA-like nucleotides that can be used to effect genetic changes in specific target genes. Other patents discussing the use of recombinagenic oligonucleobases include: U.S. Pat. Nos. 5,756,325; 5,871,984; 5,760,012; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; and WO 99/40789. Recombinagenic oligonucleobases include mixed duplex oligonucleotides, non-nucleotide containing molecules taught in Kmiec II and other molecules taught in the above-noted patents and patent publications.

Citation or identification of any reference in Section 2, or any section of this application shall not be construed as an admission that such reference is available as prior art to the present invention.

3. SUMMARY OF THE INVENTION

The present invention is directed to a non-transgenic plant or plant cell having one or more mutations in the EPSPS gene, which plant has increased resistance or tolerance to a member of the phosphonomethylglycine family and which plant exhibits substantially normal growth or development of the plant, its organs, tissues or cells, as compared to the corresponding wild-type plant or cell. The present invention is also directed to a non-transgenic plant having a mutation in the EPSPS gene, which plant is resistant to or has an increased tolerance to a member of the phosphonomethylglycine family, e.g., glyphosate, wherein the mutated EPSPS protein has substantially the same catalytic activity as compared to the wild-type EPSPS protein.

The present invention is also directed to a method for producing a non-transgenic plant having a mutated EPSPS gene that substantially maintains the catalytic activity of the wild-type protein irrespective of the presence or absence of a herbicide of the phosphonomethylglycine family. The method comprises introducing into a plant cell a recombinagenic oligonucleobase with a targeted mutation in the EPSPS gene and identifying a cell, seed, or plant having a mutated EPSPS gene.

Illustrative examples of a recombinagenic oligonucleobase is found in following patent publications, which are incorporated in their entirety be reference herein: U.S. Pat. Nos. 5,565,350; 5,756,325; 5,871,984; 5,760,012; 5,731,181; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; and WO 99/40789.

The plant can be of any species of dicotyledonous, monocotyledonous or gymnospermous plant, including any woody plant species that grows as a tree or shrub, any herbaceous species, or any species that produces edible fruits, seeds or vegetables, or any species that produces colorful or aromatic flowers. For example, the plant may be selected from a species of plant from the group consisting of canola, sunflower, tobacco, sugar beet, cotton, maize, wheat, barley, rice, sorghum, tomato, mango, peach, apple, pear, strawberry, banana, melon, potato, carrot, lettuce, onion, soya spp, sugar cane, pea, field beans, poplar, grape, citrus, alfalfa, rye, oats, turf and forage grasses, flax, oilseed rape, cucumber, morning glory, balsam, pepper, eggplant, marigold, lotus, cabbage, daisy, carnation, tulip, iris, lily, and nut producing plants insofar as they are not already specifically mentioned.

The recombinagenic oligonucleobase can be introduced into a plant cell using any method commonly used in the art, including but not limited to, microcarriers (biolistic delivery), microfibers, electroporation, microinjection.

The invention is also directed to the culture of cells mutated according to the methods of the present invention m order to obtain a plant that produces seeds, henceforth a "fertile plant", and the production of seeds and additional plants from such a fertile plant.

The invention is further directed to a method of selectively controlling weeds in a field, the field comprising plants with the disclosed EPSPS gene alterations and weeds, the method comprising application to the field of a herbicide to which the said plants have been rendered resistant.

The invention is also directed to novel mutations in the EPSPS gene that confer resistance or tolerance to a member of the phosphomethylglycine family, e.g., glyphosate, to a plant or wherein the mutated EPSPS has substantially the same enzymatic activity as compared to wild-type EPSPS.

3.1 Definitions

The invention is to be understood in accordance with the following definitions.

An oligonucleobase is a polymer of nucleobases, which polymer can hybridize by Watson-Crick base pairing to a DNA having the complementary sequence.

Nucleobases comprise a base, which is a purine, pyrimidine, or a derivative or analog thereof. Nucleobases include peptide nucleobases, the subunits of peptide nucleic acids, and morpholine nucleobases as well as nucleosides and nucleotides. Nucleosides are nucleobases that contain a pentosefuranosyl moiety, e.g., an optionally substituted riboside or 2'-deoxyriboside. Nucleosides can be linked by one of several linkage moieties, which may or may not contain a phosphorus. Nucleosides that are linked by unsubstituted phosphodiester linkages are termed nucleotides.

An oligonucleobase chain has a single 5' and 3' terminus, which are the ultimate nucleobases of the polymer. A particular oligonucleobase chain can contain nucleobases of all types. An oligonucleobase compound is a compound comprising one or more oligonucleobase chains that are complementary and hybridized by Watson-Crick base pairing. Nucleobases are either deoxyribo-type or ribo-type. Ribo-type nucleobases are pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

An oligonucleobase strand generically includes both oligonucleobase chains and segments or regions of oligonucleobase chains. An oligonucleobase strand has a 3' end and a 5' end. When a oligonucleobase strand is coextensive with a chain, the 3' and 5' ends of the strand are also 3' and 5' termini of the chain.

According to the present invention, substantially normal growth of a plant, plant organ, plant tissue or plant cell is defined as a growth rate or rate of cell division of the plant, plant organ, plant tissue, or plant cell that is at least 35%, at least 50%, at least 60%, or at least 75% of the growth rate or rate of cell division in a corresponding plant, plant organ, plant tissue or plant cell expressing the wild type EPSPS protein.

According to the present invention, substantially normal development of a plant, plant organ, plant tissue or plant cell is defined as the occurrence of one or more developmental events in the plant, plant organ, plant tissue or plant cell that are substantially the same as those occurring in a corresponding plant, plant organ, plant tissue or plant cell expressing the wild type EPSPS protein.

According to the present invention plant organs include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.

Plants are substantially "tolerant" to glyphosate when they are subjected to it and provide a dose/response curve which is shifted to the right when compared with that provided by similarly subjected non-tolerant like plant. Such dose/response curves have "dose" plotted on the X-axis and "percentage kill", "herbicidal effect", etc., plotted on the y-axis. Tolerant plants will require more herbicide than non-tolerant like plants in order to produce a given herbicidal effect. Plants which are substantially "resistant" to the glyphosate exhibit few, if any, necrotic, lytic, chlorotic or other lesions, when subjected to glyphosate at concentrations and rates which are typically employed by the agrochemical community to kill weeds in the field. Plants which are resistant to a herbicide are also tolerant of the herbicide. The terms "resistant" and "tolerant" are to be construed as "tolerant and/or resistant" within the context of the present application.

4. BRIEF DESCRIPTION OF THE FIGURES

FIG. 1A is the DNA sequence of *Arabidopsis thaliana* EPSPS gene (SEQ ID NO: 1). The bold underlined nucleotide residues are the targeted residues.

FIG. 1B is the amino acid sequence of *Arabidopsis thaliana* EPSPS protein (SEQ II) NO:2). The bold and underlined amino acid residues are the targeted residues.

FIG. 2 is a list of the *Arabidopsis thaliana* wild-type and mutant EPSPS nucleotide and amino acid sequences in the region of amino acid position 173 to 183; wild-type nucleotide sequence (SEQ ID NO: 1) and wild-type amino acid sequence (SEQ ID NO:2), mutant $A_{117}$ nucleotide sequence (SEQ ID NO:3) and amino acid sequence (SEQ ID NO:4); mutant $I_{178}$ nucleotide sequence (SEQ ID NO:5) and amino acid sequence (SEQ ID NO:6); mutant $A_{177}I_{178}$ nucleotide sequence (SEQ ID NO:7) and amino acid sequence (SEQ ID NO:8); mutant $I_{178}S_{182}$ nucleotide sequence (SEQ ID NO:9) and amino acid sequence (SEQ ID NO: 10); mutant $A_{177}S_{182}$ nucleotide sequence (SEQ ID NO:11) and amino acid sequence (SEQ ID NO:12); mutant $A_{177}I_{178}S_{182}$ nucleotide sequence (SEQ TD NO:13) and amino acid sequence (SEQ ID NO:14); mutant $V_{177}S_{182}$ nucleotide sequence (SEQ ID NO: 15) and amino acid sequence (SEQ ID NO:16); mutant $L_{178}S_{182}$ nucleotide sequence (SEQ ID NO:17) and amino acid sequence (SEQ ID NO:18); mutant $A_{177}V_{178}$ nucleotide sequence (SEQ ID NO:19) and amino acid sequence (SEQ ID NO:20); mutant $A_{177}L_{182}$ nucleotide sequence (SEQ ID NO:21) and amino acid sequence (SEQ ID NO:22).

FIG. 3A-C is an alignment of the DNA of *Arabidopsis thaliana* EPSPS gene performed by DNAStar (LaserGene), (SEQ ID NO: 1) with the nucleotide sequences of *Brassica napus* (SEQ ID NO:23); *Petunia hybrida* (SEQ ID NO:24); and *Zea mays* (SEQ ID NO:25) EPSPS gene. The sequences are aligned using J. Hein method with weighted residue weight table.

FIG. 4 is an alignment of the *Arabidopsis thaliana* EPSPS amino acid sequence (SEQ 1D NO:2) with the *Brassica napus* (SEQ ID NO:26); *Petunia hybrida* (SEQ ID NO:27); and *Zea mays* (SEQ ID NO:28) EPSPS amino acid sequences. The sequences are aligned using J. Hein method with weighted residue weight table.

FIG. 5 is a list of the mutagenesis primers used, with the targeted codons in bold characters (mutant primer $A_{177}$ (SEQ ID NO:29); mutant primer $I_{178}$ (SEQ ID NO:30); mutant primer $A_{177}I_{178}$ (SEQ ID NO:31); mutant primer $I_{178}S_{182}$ (SEQ ID NO:32); mutant primer $A_{177}S_{182}$ (SEQ ID NO:34); mutant primer $A_{177}I_{178}S_{182}$ (SEQ ID NO:35); mutant primer $V_{177}S_{182}$ (SEQ ID NO:35); mutant primer $L_{178}S_{182}$ (SEQ ID NO:36); mutant primer $A_{177}V_{178}$ (SEQ ID NO:37); and mutant primer $A_{177}L_{182}$ (SEQ ID NO:38)).

Figure 6:
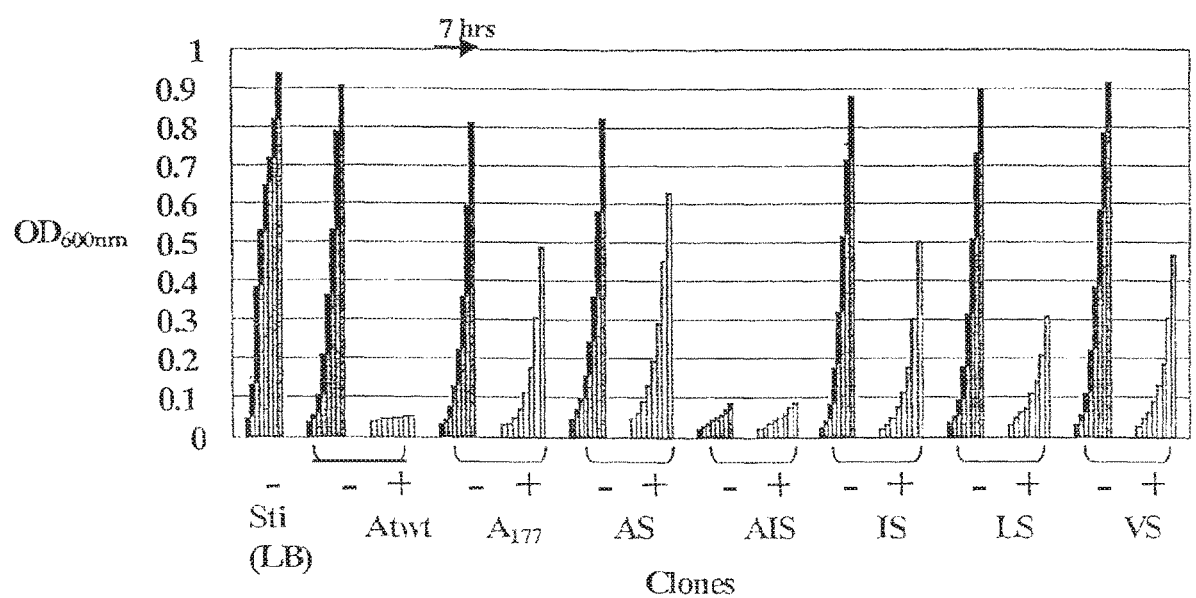

FIG. 6 is the growth measured by optical density at 600 nm of *Arabidopsis* clones in the presence (+) and absence (−) of 17 mM glyphosate.

Figure 7:
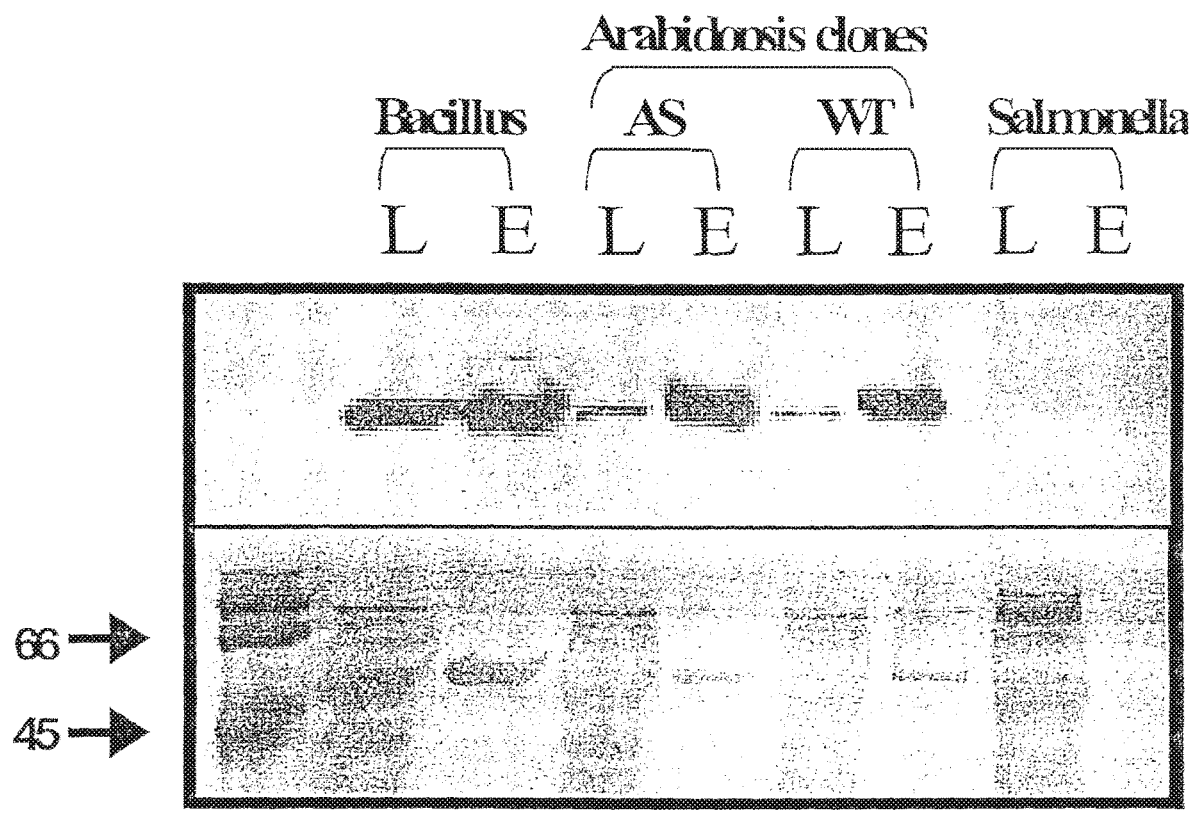

FIG. 7 (top panel) is a western blot showing the expression of His-tagged *Bacillus*, *Arabidopsis* wild type (WT) and mutant (AS) EPSPS proteins isolated from cell lysates (L) and eluates (E). Untransformed *Salmonella* as a negative control shows no EPSPS expression. The bottom panel is a silver-stained duplicate gel.

5. DETAILED DESCRIPTION OF THE INVENTION

The present invention is directed to a non-transgenic plant or plant cell having a mutation in the EPSPS gene, which plant has increased resistance or tolerance to a member of the phosphonomethylglycine family and which plant exhibits substantially normal growth or development of the plant, its organs, tissues or cells, as compared to the corresponding wild-type plant or cell. The present invention is also directed to a non-transgenic plant having a mutation in the EPSPS gene, which plant is resistant to or has an increased tolerance to a member of the phosphonomethylglycine family, e.g., glyphosate, wherein the mutated EPSPS protein has substantially the same catalytic activity as compared to the wild-type EPSPS protein.

The present invention is also directed to a method for producing a non-transgenic plant having a mutated EPSPS gene that substantially maintains the catalytic activity of the wild-type protein irrespective of the presence or absence of a herbicide of the phosphonomethylglycine family. The method comprises introducing into a plant cell a recombinagenic oligonucleobase with a targeted mutation in the EPSPS gene and identifying a cell, seed, or plant having a mutated EPSPS gene.

Illustrative examples of a recombinagenic oligonucleobase is found in following patent publications, which are incorporated in their entirety be reference herein: U.S. Pat. Nos. 5,565,350; 5,756,325; 5,871,984; 5,760,012; 5,731,181; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; and WO 99/40789.

The plant can be of any species of dicotyledonous, monocotyledonous or gymnospermous plant, including any woody plant species that grows as a tree or shrub, any herbaceous species, or any species that produces edible fruits, seeds or vegetables, or any species that produces colorful or aromatic flowers. For example, the plant may be selected from a species of plant from the group consisting of canola, sunflower, tobacco, sugar beet, cotton, maize, wheat, barley, rice, sorghum, tomato, mango, peach, apple, pear, strawberry, banana, melon, potato, carrot, lettuce, onion, soya spp, sugar cane, pea, field beans, poplar, grape, citrus, alfalfa, rye, oats, turf and forage grasses, flax, oilseed rape, cucumber, morning glory, balsam, pepper, eggplant, marigold, lotus, cabbage, daisy, carnation, tulip, iris, lily, and nut producing plants insofar as they are not already specifically mentioned.

The recombinagenic oligonucleobase can be introduced into a plant cell using any method commonly used in the art, including but not limited to, microcarriers (biolistic delivery), microfibers, electroporation, microinjection.

The invention is also directed to the culture of cells mutated according to the methods of the present invention in order to obtain a plant that produces seeds, henceforth a "fertile plant", and the production of seeds and additional plants from such a fertile plant.

The invention is further directed to a method of selectively controlling weeds in a field, the field comprising plants with the disclosed EPSPS gene alterations and weeds, the method comprising application to the field of a herbicide to which the said plants have been rendered resistant.

The invention is also directed to novel mutations in the EPSPS gene that confer resistance or tolerance to a member of the phosphonomethylglycine family, e.g., glyphosate, to a plant or wherein the mutated EPSPS has substantially the same enzymatic activity as compared to wild-type EPSPS.

5.1 Recombinagenic Oligonucleobases

The invention can be practiced with recombinagenic oligonucleobases having the conformations and chemistries described in U.S. Pat. No. 5,565,350 to Kmiec (Kmiec I) and U.S. Pat. No. 5,731,181 (Kmiec II) gene, which are hereby incorporated by reference. Kmiec I teaches a method for introducing specific genetic alterations into a target gene. The recombinagenic oligonucleobases in Kmiec I and/or Kmiec II contain two complementary strands, one of which contains at least one segment of RNA-type nucleotides (an "RNA segment") that are base paired to DNA-type nucleotides of the other strand.

Kmiec II discloses that purine and pyrimidine base-containing non-nucleotides can be substituted for nucleotides. U.S. Pat. Nos. 5,756,325; 5,871,984; 5,760,012; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; and WO 99/40789, which are each hereby incorporated in their entirety, disclose additional recombinagenic molecules that can be used for the present invention. The term "recombinagenic oligonucleobase" is used herein to denote the molecules that can be used in the methods of the present invention and include mixed duplex oligonucleotides, non-nucleotide containing molecules taught in Kmiec II, single stranded oligodeoxynucleotides and other recombinagenic molecules taught in the above noted patents and patent publications.

In one embodiment, the recombinagenic oligonucleobase is a mixed duplex oligonucleotide in which the RNA-type nucleotides of the mixed duplex oligonucleotide are made RNase resistant by replacing the 2'-hydroxyl with a fluoro, chloro or bromo functionality or by placing a substituent on the 2'-O. Suitable substituents include the substituents taught by the Kmiec II. Alternative substituents include the substituents taught by U.S. Pat. No. 5,334,711 (Sproat) and the substituents taught by patent publications EP 629 387 and EP 679 657 (collectively, the Martin Applications), which are hereby incorporated by reference. As used herein, a 2'-fluoro, chloro or bromo derivative of a ribonucleotide or a ribonucleotide having a 2'-OH substituted with a substituent described in the Martin Applications or Sproat is termed a "2'-Substituted Ribonucleotide." As used herein the term "RNA-type nucleotide" means a 2'-hydroxyl or 2'-Substituted Nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a 2'-H, which can be linked to other nucleotides of a MDON by an unsubstituted phosphodiester linkage or any of the non-natural linkages taught by Kmiec I or Kmiec II.

In a particular embodiment of the present invention, the recombinagenic oligonucleobase is a mixed duplex oligonucleotide that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-Substituted Nucleotide. Particular preferred embodiments of 2'-Substituted Ribonucleotides are 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropropyloxy substituted ribonucleotides. More preferred embodiments of 2'-Substituted Ribonucleotides are 2'-fluoro, 2'-methoxy, 2'-methoxyethyloxy, and 2'-allyloxy substituted nucleotides. In another embodiment the mixed duplex oligonucleotide is linked by unsubstituted phosphodiester bonds.

Although mixed duplex oligonucleotide having only a single type of 2'-substituted RNA-type nucleotide are more conveniently synthesized, the methods of the invention can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses such an "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides preferably have fewer than 100 nucleotides and more preferably fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target EPSPS gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene. Alternatively, the heterologous region can also contain an insertion or one, two, three or of five or fewer nucleotides. Alternatively, the sequence of the mixed duplex oligonucleotide may differ from the sequence of the target gene only by the deletion of one, two, three, or five or fewer nucleotides from the mixed duplex oligonucleotide. The length and position or the heterologous region is, in this case, deemed to be the length of the deletion, even though no nucleotides of the mixed duplex oligonucleotide are within the heterologous region. The distance between the fragments of the target gene that are complementary to the two homologous regions is identically the length of the heterologous region when a substitution or substitutions is intended. When the heterologous region contains an insertion, the homologous regions are thereby separated in the mixed duplex oligonucleotide farther than their complementary homologous fragments are in the gene, and the converse is applicable when the heterologous region encodes a deletion.

The RNA segments of the mixed duplex oligonucleotides are each a part of a homologous region, i.e., a region that is identical in sequence to a fragment of the target gene, which segments together preferably contain at least 13 RNA-type nucleotides and preferably from 16 to 25 RNA-type nucleotides or yet more preferably 18-22 RNA-type nucleotides or most preferably 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

The change to be introduced into the target EPSPS gene is encoded by the heterologous region. The change to be introduced into the EPSPS gene may be a change in one or more bases of the EPSPS gene sequence or the addition or deletion of one or more bases.

In another embodiment of the present invention, the recombinagenic oligonucleobase is a single stranded oligodeoxynucleotide mutational vector or SSOMV, which is disclosed in International Patent Application PCT/US00/23457, which is incorporated by reference in its entirety. The sequence of the SSOMV is based on the same principles as the mutational vectors described in U.S. Pat. Nos. 5,756,325; 5,871,984; 5,760,012; 5,888,983; 5,795,972; 5,780,296; 5,945,339; 6,004,804; and 6,010,907 and in International Publication Nos. WO 98/49350; WO 99/07865; WO 99/58723; WO 99/58702; and WO 99/40789. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region can cause a substitution. Alternatively, the homolgous regions in the SSOMV can be contiguous to each other, while the regions in the target gene having the same sequence are separated by one, two or more nucleotides. Such a SSOMV causes a deletion from the target gene of the nucleotides that are absent from the SSOMV. Lastly, the sequence of the target gene that is identical to the homologous regions may be adjacent in the target gene but separated by one two or more nucleotides in the sequence of the SSOMV. Such an SSOMV causes an insertion in the sequence of target gene.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent, see supra. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotide be a pyrimidine. To the extent that is consistent with achieving the desired functional result it is preferred that both the mutator nucleotide and the targeted nucleotide in the complementary strand be pyrimidines. Particularly preferred are SSOMV that encode transversion mutations, i.e., a C or T mutator nucleotide is mismatched, respectively, with a C or T nucleotide in the complementary strand.

In addition to the oligodeoxynucleotide the SSOMV can contain a 5' blocking substituent that is attached to the 5' terminal carbons through a linker. The chemistry of the linker is not critical other than its length, which should preferably be at least 6 atoms long and that the linker should be flexible. A variety of non-toxic substituents such as biotin, cholesterol or other steroids or a non-intercalating cationic fluorescent dye can be used. Particularly preferred as reagents to make SSOMV are the reagents sold as Cy3™ and Cy5™ by Glen Research, Sterling Va., which are blocked phosphoroamidites that upon incorporation into an oligonucleotide yield 3,3,3',3'-tetramethyl N,N'-isopropyl substituted indomonocarbocyanine and indodicarbocyanine dyes, respectively. Cy3 is the most preferred. When the indocarbocyanine is N-oxyalkyl substituted it can be conveniently linked to the 5' terminal of the oligodeoxynucleotide through as a phosphodiester with a 5' terminal phosphate. The chemistry of the dye linker between the dye and the oligodeoxynucleotide is not critical and is chosen for synthetic convenience. When the commercially available Cy3 phosphoramidite is used as directed the resulting 5' modification consists of a blocking substituent and linker together which are a N-hydroxypropyl, N'-phosphatidylpropyl 3,3,3',3'-tetramethyl indomonocarbocyanine.

In the preferred embodiment the indocarbocyanine dye is tetra substituted at the 3 and 3' positions of the indole rings. Without limitation as to theory these substitutions prevent the dye from being an intercalating dye. The identity of the substituents at these positions are not critical. The SSOMV can in addition have a 3' blocking substituent. Again the chemistry of the 3' blocking substituent is not critical.

5.2 the Location and Type of Mutation Introduced into the EPSPS Gene

In one embodiment of the present invention, the *Arabidopsis thaliana* EPSPS gene (see FIG. 1A) and corresponding EPSPS enzyme (see FIG. 1B) comprises a mutation at one or more amino acid residues selected from the group consisting of $Leu_{173}$, $Gly_{177}$, $Thr_{178}$, $Ala_{179}$, $Met_{180}$, $Arg_{181}$, $Pro_{182}$, $Ser_{98}$, $Ser_{255}$, and $Leu_{198}$, or at an analogous position in an EPSPS paralog, and the mutation results in one or more of the following amino acid substitutions in the EPSPS enzyme in comparison with the wild-type sequence:
  (i) $Leu_{173}$—Phe
  (ii) $Gly_{177}$—Ala or Ile
  (iii) $Thr_{178}$—Ile or Val or Leu
  (iv) $Ala_{179}$—Gly
  (v) $Met_{180}$—Cys
  (vi) $Arg_{181}$—Leu or Ser
  (vii) $Pro_{182}$—Leu or Ser
  (viii) $Ser_{98}$—Asp
  (ix) $Ser_{255}$—Ala
  (x) $Leu_{198}$—Lys.

In another embodiment of the present invention, within the EPSPS gene product, the amino acid residue to be changed is Leu within the contiguous sequence Leu-Tyr-Leu-Gly-Asn (SEQ ID NO:29) and is changed to Phe; or the amino acid residue to be changed is Gly within the contiguous sequence Asn-Ala-Gly-Thr-Ala (SEQ ID NO:30) and is changed to Ala or Ile; or the amino acid to be changed is Thr within the contiguous sequence Ala-Gly-Thr-Ala-Met (SEQ ID NO:31) and is changed to Ile, Val or Leu; or the amino acid to be changed is Ala within the contiguous sequence Gly-Thr-Ala-Met-Arg (SEQ ID NO:32) and is changed to Gly; or the amino acid to be changed is Met within the contiguous sequence Thr-Ala-Met-Arg-Pro (SEQ ID NO:33) and is changed to Cys; or the amino acid to be changed is Arg within the contiguous sequence Ala-Met-Arg-Pro-Leu (SEQ ID NO:34) and is changed to Leu or Ser; or the amino acid to be changed is Pro within the contiguous sequence Met-Arg-Pro-Leu-Thr (SEQ ID NO:35) and is changed to Leu or Ser; or the amino acid to be changed is Ser within a contiguous Pro-Gly-Ser-Lys-Ser (SEQ ID NO:36) and is changed to Asp; or the amino acid to be changed is Ser within the contiguous sequence Ile-Ser-Ser-Gln-Tyr (SEQ ID NO:37) and is changed to Ala; or the amino acid to be changed is Leu within the contiguous sequence Tyr-Val-Leu-Asp-Gly (SEQ ID NO:38) and is changed to Lys. In other embodiments, one or more of the foregoing changes can be made in the EPSPS amino acid sequence.

Alternatively, and/or additionally, the mutation may result in the replacement of any amino acid at positions corresponding to 256, 284-288 and 353-356 with respect to the EPSPS protein depicted in FIG. 1B (SEQ ID NO. 2).

In specific embodiments of the present invention, the EPSPS gene is mutated at amino acid position 177 in which Gly is replaced by Ala. Another specific embodiment is the substitution of Thr at amino acid position 178 by Ile. A further specific embodiment comprises a mutation at amino acid position 177 in which Gly is replaced by Ala, plus the additional substitution of Thr at amino acid position 178 by Ile. Other specific embodiments of the present invention are directed to mutations at amino acid position 178, in which Thr is replaced by Ile, plus the additional mutation at position 182, in which Pro is replaced by Ser. Other embodiments include the substitution of Gly at amino acid position 177 by Ala, plus the additional mutation at amino acid position 182, in which Pro is substituted by Ser. Other mutated EPSPS sequences comprise the substitution of Gly at position 177 by Ala, plus the substitution at position 178, in which Thr is replaced by Ile, plus the additional substitution of Pro at amino acid position 182 by Ser. Another embodiment is the substitution of Thr at amino acid position 178 by Val and the additional mutation at amino acid position 182, in which Pro is replaced by Ser. A further specific embodiment includes the substitution of Thr at position 178 by Leu, plus the mutation at amino acid position 182, in which Pro is replaced by Ser. A further embodiment includes, the substitution at amino acid position 177 in which Gly is replaced by Ala, plus the substitution of Thr at position 178 by Val. The invention also embodies the substitution at amino acid position 177 in which Gly is replaced by Ala, plus the replacement of Thr at amino acid position 178 by Leu (see FIG. 2).

The foregoing mutations in the EPSPS gene were described using the *Arabidopsis thaliana* EPSPS gene (SEQ ID NO: 1) and protein (SEQ ID NO:2). The present invention also encompasses mutant EPSPS genes of other species (paralogs). However, due to variations in the EPSPS genes of different species, the number of the amino acid residue to be changed in one species may be different in another species. Nevertheless, the analogous position is readily identified by one of skill in the art by sequence homology. For example, FIG. 3A-C shows the aligned nucleotide sequences and FIG. 4 shows the aligned amino acid sequences of four paralogs of the EPSPS gene, *Arabidopsis thaliana*, *Zea mays*, *Petunia hybrida*, and *Brassica napus*. Thus, the analogous positions in *Zea mays* are $Leu_{97}$, $Gly_{101}$, $Thr_{102}$, $Ala_{103}$, $Met_{104}$, $Arg_{105}$, $Pro_{106}$, $Ser_{23}$, $Ser_{179}$ and $Leu_{122}$. Thus, the *Zea mays* EPSPS amino acid sequence is mutated at one or more of the following amino acid positions and results in one or more of the following substitutions:
  (i) $Leu_{97}$—Phe
  (ii) $Gly_{101}$—Ala or Ile
  (iii) $Thr_{102}$—Ile or Val or Leu
  (iv) $Ala_{103}$—Gly
  (v) $Met_{104}$—Cys
  (vi) $Arg_{105}$—Leu or Ser (vii) $Pro_{106}$—Leu or Ser
(viii) $Ser_{23}$—Asp
(ix) $Ser_{179}$—Ala
(x) $Leu_{122}$—Lys.

In another embodiment of the present invention, within the *Zea mays* EPSPS gene product the amino acid residue to be changed is Leu within the contiguous sequence Leu-Phe-Leu-Gly-Asn (SEQ ID NO:39) and is changed to Phe; or the amino acid residue to be changed is Gly within the contiguous sequence Asn-Ala-Gly-Thr-Ala (SEQ ID NO:30) and is changed to Ala or Ile; or the amino acid to be changed is Thr within the contiguous sequence Ala-Gly-Thr-Ala-Met (SEQ ID NO:31) and is changed to Ile, Val or Leu; or the amino acid to be changed is Ala within the contiguous sequence Gly-Thr-Ala-Met-Arg (SEQ ID NO:32) and is changed to Gly; or the amino acid to be changed is Met within the contiguous sequence Thr-Ala-Met-Arg-Pro (SEQ ID NO:33) and is changed to Cys; or the amino acid to be changed is Arg within the contiguous sequence Ala-Met-Arg-Pro-Leu (SEQ ID NO:34) and is changed to Leu or Ser; or the amino acid to be changed is Pro within the contiguous sequence Met-Arg-Pro-Leu-Thr (SEQ ID NO:35) and is changed to Leu or Ser; or the amino acid to be changed is Ser within a contiguous Pro-Gly-Ser-Lys-Ser (SEQ ID NO:36) and is changed to Asp; or the amino acid to be changed is Ser within the contiguous sequence Ile-Ser-Ser-Gln-Tyr (SEQ ID NO:37) and is changed to Ala; or the amino acid to be changed is Leu within the contiguous sequence Tyr-Val-Leu-Asp-Gly (SEQ ID NO:38) and is changed to Lys. In other embodiments, one or more of the foregoing changes can be made in the EPSPS amino acid sequence.

In *Brassica napus*, the analogous amino acid positions are $Leu_{169}$, $Gly_{173}$, $Thr_{174}$, $Ala_{175}$, $Met_{176}$, $Arg_{177}$, $Pro_{178}$, $Ser_{94}$, $Ser_{251}$ and $Leu_{194}$. Thus, the *Brassica napus* EPSPS amino acid sequence is mutated at one or more of the following amino acid positions and results in one or more of the following substitutions:

(i) $Leu_{169}$—Phe
(ii) $Gly_{173}$—Ala or Ile
(iii) $Thr_{174}$—Ile or Val or Leu
(iv) $Ala_{175}$—Gly
(v) $Met_{176}$—Cys
(vi) $Arg_{177}$—Leu or Ser
(vii) $Pro_{178}$—Leu or Ser
(viii) $Ser_{94}$—Asp
(ix) $Ser_{251}$—Ala
(x) $Leu_{194}$—Lys In another embodiment of the present invention, within the *Brassica napus* EPSPS gene product the amino acid residue to be changed is Leu within the contiguous sequence Leu-Tyr-Leu-Gly-Asn (SEQ ID NO:29) and is changed to Phe; or the amino acid residue to be changed is Gly within the contiguous sequence Asn-Ala-Gly-Thr-Ala (SEQ ID NO:30) and is changed to Ala or Ile; or the amino acid to be changed is Thr within the contiguous sequence Ala-Gly-Thr-Ala-Met (SEQ ID NO:31) and is changed to Ile, Val or Leu; or the amino acid to be changed is Ala within the contiguous sequence Gly-Thr-Ala-Met-Arg (SEQ ID NO:32) and is changed to Gly; or the amino acid to be changed is Met within the contiguous sequence Thr-Ala-Met-Arg-Pro (SEQ ID NO:33) and is changed to Cys; or the amino acid to be changed is Arg within the contiguous sequence Ala-Met-Arg-Pro-Leu (SEQ ID NO:34) and is changed to Leu or Ser; or the amino acid to be changed is Pro within the contiguous sequence Met-Arg-Pro-Leu-Thr (SEQ ID NO:35) and is changed to Leu or Ser; or the amino acid to be changed is Ser within a contiguous Pro-Gly-Ser-Lys-Ser (SEQ ID NO:36) and is changed to Asp; or the amino acid to be changed is Ser within the contiguous sequence Ile-Ser-Ser-Gln-Tyr (SEQ ID NO:37) and is changed to Ala; or the amino acid to be changed is Leu within the contiguous sequence Tyr-Val-Leu-Asp-Gly (SEQ ID NO:38) and is changed to Lys. In other embodiments, one or more of the foregoing changes can be made in the EPSPS amino acid sequence.

In *Petunia hybrida* the analogous positions are $Leu_{169}$, $Gly_{173}$, $Thr_{1747}$, $Ala_{175}$, $Met_{176}$, $Arg_{177}$, $Pro_{178}$, $Ser_{94}$, $Ser_{251}$ and $Leu_{194}$. Thus, the *Petunia hybrida* EPSPS amino acid sequence is mutated at one or more of the following amino acid positions and results in one or more of the following substitutions:

(i) $Leu_{169}$—Phe
(ii) $Gly_{173}$—Ala or Ile
(iii) $Thr_{174}$—Ile or Val or Leu
(iv) $Ala_{175}$—Gly
(v) $Met_{176}$—Cys
(vi) $Arg_{177}$—Leu or Ser
(vii) $Pro_{178}$—Leu or Ser
(viii) $Ser_{94}$—Asp
(ix) $Ser_{251}$—Ala
(x) $Leu_{194}$—Lys In another embodiment of the present invention, within the *Petunia hybrida* EPSPS gene product the amino acid residue to be changed is Leu within the contiguous sequence Leu-Phe-Leu-Gly-Asn (SEQ ID NO:39) and is changed to Phe; or the amino acid residue to be changed is Gly within the contiguous sequence Asn-Ala-Gly-Thr-Ala (SEQ ID NO:30) and is changed to Ala or Ile; or the amino acid to be changed is Thr within the contiguous sequence Ala-Gly-Thr-Ala-Met (SEQ ID NO:31) and is changed to Ile, Val or Leu; or the amino acid to be changed is Ala within the contiguous sequence Gly-Thr-Ala-Met-Arg (SEQ ID NO:32) and is changed to Gly; or the amino acid to be changed is Met within the contiguous sequence Thr-Ala-Met-Arg-Pro (SEQ ID NO:33) and is changed to Cys; or the amino acid to be changed is Arg within the contiguous sequence Ala-Met-Arg-Pro-Leu (SEQ ID NO:34) and is changed to Leu or Ser; or the amino acid to be changed is Pro within the contiguous sequence Met-Arg-Pro-Leu-Thr (SEQ ID NO:35) and is changed to Leu or Ser; or the amino acid to be changed is Ser within a contiguous Pro-Gly-Ser-Lys-Ser (SEQ ID NO:36) and is changed to Asp; or the amino acid to be changed is Ser within the contiguous sequence Ile-Ser-Ser-Gln-Tyr (SEQ ID NO:37) and is changed to Ala; or the amino acid to be changed is Leu within the contiguous sequence Tyr-Val-Leu-Asp-Gly (SEQ II) NO:38) and is changed to Lys. In other embodiments, one or more of the foregoing changes can be made in the EPSPS amino acid sequence.

5.3 the Delivery of Recombinagenic Oligonucleobases into Plant Cells

Any commonly known method can be used in the methods of the present invention to transform a plant cell with a recombinagenic oligonucleobases. Illustrative methods are listed below.

5.3.1 Microcarriers and Microfibers

The use of metallic microcarriers (microspheres) for introducing large fragments of DNA into plant cells having cellulose cell walls by projectile penetration is well known to those skilled in the relevant art (henceforth biolistic delivery). U.S. Pat. Nos. 4,945,050; 5,100,792 and 5,204,253 describe general techniques for selecting microcarriers and devices for projecting them.

Specific conditions for using microcarriers in the methods of the present invention are described in International Publication WO 99/07865. In an illustrative technique, ice cold microcarriers (60 mg/ml), mixed duplex oligonucleotide (60 mg/ml) 2.5 M $CaCl_2$ and 0.1 M spermidine are added in that order; the mixture gently agitated, e.g., by vortexing, for 10 minutes and let stand at room temperature for 10 minutes, whereupon the microcarriers are diluted in 5 volumes of ethanol, centrifuged and resuspended in 100% ethanol. Good results can be obtained with a concentration in the adhering solution of 8-10 µg/µl microcarriers, 14-17 µg/ml mixed duplex oligonucleotide, 1.1-1.4 M $CaCl_2$ and 18-22 mM spermidine. Optimal results were observed under the conditions of 8 µg/µl microcarriers, 16.5 µg/ml mixed duplex oligonucleotide, 1.3 M $CaCl_2$ and 21 mM spermidine.

Recombinagenic oligonucleobases can also be introduced into plant cells for the practice of the present invention using microfibers to penetrate the cell wall and cell membrane. U.S. Pat. No. 5,302,523 to Coffee et al. describes the use of 30×0.5 µm and 10×0.3 µm silicon carbide fibers to facilitate transformation of suspension maize cultures of Black Mexican Sweet. Any mechanical technique that can be used to introduce DNA for transformation of a plant cell using microfibers can be used to deliver recombinagenic oligonucleobases for transmutation.

An illustrative technique for microfiber delivery of a recombinagenic oligonucleobase is as follows: Sterile microfibers (2 µg) are suspended in 150 µl of plant culture medium containing about 10 µg of a mixed duplex oligonucleotide. A suspension culture is allowed to settle and equal volumes of packed cells and the sterile fiber/nucleotide suspension are vortexed for 10 minutes and plated. Selective media are applied immediately or with a delay of up to about 120 hours as is appropriate for the particular trait.

5.3.2 Protoplast Electroporation

In an alternative embodiment, the recombinagenic oligonucleobases can be delivered to the plant cell by electroporation of a protoplast derived from a plant part. The protoplasts are formed by enzymatic treatment of a plant part, particularly a leaf, according to techniques well known to those skilled in the art. See, e.g., Gallois et al., 1996, in Methods in Molecular Biology 55:89-107, Humana Press, Totowa, N.J.; Kipp et al., 1999, in Methods in Molecular Biology 133:213-221, Humana Press, Totowa, N.J. The protoplasts need not be cultured in growth media prior to electroporation. Illustrative conditions for electroporation are $3×10^5$ protoplasts in a total volume of 0.3 ml with a concentration of recombinagenic oligonucleobase of between 0.6-4 µg/mL.

5.3.3 Whiskers and Microinjection

In yet another alternative embodiment, the recombinagenic oligonucleobase can be delivered to the plant cell by whiskers or microinjection of the plant cell. The so called whiskers technique is performed essentially as described in Frame et al., 1994, Plant J. 6:941-948. The recombinagenic oligonucleobase is added to the whiskers and used to transform the plant cells. The recombinagenic oligonucleobase may be co-incubated with plasmids comprising sequences encoding proteins capable of forming recombinase complexes in plant cells such that recombination is catalyzed between the oligonucleotide and the target sequence in the EPSPS gene.

5.4 Selection of Glyphosate Resistant Plants

Plants or plant cells can be tested for resistance or tolerance to a herbicide using commonly known methods in the art, e.g., by growing the plant or plant cell in the presence of a herbicide and measuring the rate of growth as compared to the growth rate in the absence of the herbicide.

6. EXAMPLE

The following experiments demonstrate the production of mutant *Arabidopsis thaliana* EPSPS genes which are resistant to the herbicide glyphosate and which allows the plant cells to maintain a growth rate

6.1 Material and Methods

6.1.1 Isolation of *Arabidopsis thaliana* EPSPS cDNA

A 1.3 kb DNA fragment was amplified by PCR from an *Arabidopsis* cDNA library using the primers AtEXPEXPM1 and AtEXPEXP2CM-2. The two primers were designed to amplify the cDNA from the mature peptide to the termination codon. The 5' primer AtEXPEXPM1 contains an XbaI site (underlined) and the 3' primer AtEXPEXP2CM-2 contains a BglII site (underlined), sites which will be of use for cloning of the fragment into the expression vector.

```
AtEXPEXPM1
                                          (SEQ ID NO: 40)
5'-GCTCTAGAGAAAGCGTCGGAGATTGTACTT-3'

AtEXPEXP2CM-2
                                          (SEQ ID NO: 41)
5'-GCAGATCTGAGCTCTTAGTGCTTTGTGATTCTTTCAAGTAC-3'
```

The PCR band was excised from the agarose gel and purified (GeneClean, Biol). Its sequence was then confirmed as the mature peptide sequence of *Arabidopsis thaliana* EPSPS gene.

6.1.2 Preparation of the Expression Vector

The EPSPS coding region of the AroE *Bacillus subtilis* gene was obtained by PCR using the following primers:

```
BsAroE5'Xba
                                          (SEQ ID NO: 42)
5'-GCGTCTAGAAAAACGAGATAAGGTGCAG-3'
and BsAroE3'BamHI
                                          (SEQ ID NO: 43)
5'-GCGGATCCTCAGGATTTTTTCGAAAGCTTATTTAAATG-3'.
```

The PCR fragment, lacking an initiation codon (ATG), was cloned in-frame to the pACLacIMH6RecA vector by replacing the ORF of RecA by digesting with XbaI and BamHI. PACLacMH6RecA contained the LacI region of Pet21 at positions 1440 to 3176, the MH6 RecA at positions 3809 to 5188, chloramphenicol resistance gene at positions 5445-218 (5446 to 5885 and 1 to 218), and the p15A origin of replication at positions 581 to 1424. The coding region of RecA gene was cloned from *E. coli* in-frame with the start codon and 6 histidine linker (MH6) behind the LacZ promoter of pUC19.

6.1.3 Cloning of the *Arabidopsis* EPSPS Gene into Bacterial Expression Vector The *Arabidopsis* 1.3 kb PCR fragment was digested with XbaI and BamHI (compatible with BglII) and cloned into the plasmid pACYCLacIMH6EPSPS, in place of the *Bacillus* gene.

The clones obtained (selected on chloramphenicol) were then sequenced and confirmed positive. One of the confirmed clones (pAtEPS-12) was selected and the junctions between the cDNA and the cloning plasmid were also confirmed to be identical to the expected sequences.

6.1.4 Novel Point Mutations in the EPSPS Gene

Ten different mutants of the *Arabidopsis thaliana* EPSPS gene were designed, (see FIG. 2). For the mutagenesis experiments, PCR primers were designed with one, two or three mutations. The PCR reactions were performed using a regular flanking primer (5'ATEPS-198: 5'-GAAAGCGTCG-GAGATTGTAC-3' (SEQ ID NO:44)) and one of the mutation-carrying primers (see FIG. 5).

The 353 bp PCR fragments obtained were purified (Qiagen PCR Purification kit) and their sequence confirmed. The fragments were then digested with PstI (underlined in the primer sequences) and BamHI and ligated to the pAtEPS-12 vector, which had itself been previously digested with PstI and BamHI.JM109 (Promega) competent cells were used for the transformation and plated onto chloramphenicol-containing LB plates. Clones from each mutagenesis experiment were then isolated and their sequence confirmed.

6.1.5 Glyphosate Resistance Assays

Electrocompetent cells of SA4247, a LacZ-*Salmonella typhi* strain, were prepared according to well known procedures (see Current Protocols in Molecular Biology, (Wiley and Sons, Inc.)). 30 µl of SA4247 competent cells were electroporated with 20 ng of each plasmid DNA encoding *Arabidopsis* wild-type and mutant EPSPS proteins, *Bacillus* wild-type EPSPS, along with a mock transfection as a control. The settings for electroporation were 25 µF, 2.5 KV and 200 ohms. After electroporation, the cells were transferred into 15 mls culture tube and supplemented with 970 µl of SOC medium. The cultures were incubated for 1½ hours at 37° C. at 225 rpm. 50 µl of each culture were plated onto LB plates containing 17 µg/ml chloramphenicol (in duplicates) and incubated overnight at 37° C. On the following day, 5 colonies of each plate were picked and transferred onto M9 plates and incubated overnight at 37° C.

Colonies from the overnight incubation on solid M9 were inoculated into 4 ml of liquid M9 medium and grown overnight at 37° C. On the following day, 25 ml of liquid M9 medium containing chloramphenicol, IPTG and 17 mM or 0 mM Glyphosate (Aldrich, 33775-7) were inoculated with 1-2 mls of each overnight culture (in duplicates), the starting OD (at 600 nm) was measured and all the cultures were normalized to start at the same OD. An OD measurement was taken every hour for seven hours. As a control of the bacterial growth, a culture of untransformed *Salmonella* was also inoculated into plain LB medium. In two independent experiments, the clones $A_{177}I_{178}$, $A_{177}V_{178}$, $A_{177}L_{178}$ and $I_{177}$ did not grow in M9 medium, therefore the glyphosate-resistance assays could not be performed on them.

6.1.7 Isolation and Purification of the Expressed Protein from Bacterial Clones One milliliter of overnight culture of each of the bacterial clones is inoculated into 100 ml of liquid LB medium containing chloramphenicol. The cells were allowed to grow at 37° C. until they reached an OD of 0.5-0.7 (approximately 3½ hours). IPTG was then added to the cultures to a concentration of 1.0 mM. The cells were grown five additional hours. They were then pelleted at 4000 rpm for 20 minutes at 4° C.

The isolation and the purification of the His-tagged proteins were performed following the Qiagen Ni-NTA Protein Purification System: Cell lysates and eluates were run in duplicates on 12.5% acrylamide gels. One of the gels was silver-stained for immediate visualization, the second gel was transferred onto Millipore Immobilon-P membrane, and blocked overnight in 5% milk in TBS-T. The membrane was then exposed to Anti-His primary antibody solution (Amersham Pharmacia biotech, cat #37-4710), followed by exposure to Anti-Mouse-IgG secondary antibody solution. (NIF825, from Amersham Pharmacia biotech ECL Western blotting analysis system, cat # RPN2108). Washes and detection reactions were performed according to the manufacturer instructions. Autoradiograms were developed after 5 minutes exposure.

6.2 Results

Cells containing a mutation in the EPSPS gene produced cells that were both resistant to the herbicide glyphosate and that had a substantially similar growth rate in the absence or presence of glyphosate, as compared to the wild-type cells, irrespective of the presence of glyphosate (see FIG. 6).

It was also demonstrated that the *Arabidopsis* clones containing a mutant EPSPS gene expressed the mutant protein at substantially the same level as the wild-type protein (see FIG. 7).

The invention claimed and described herein is not to be limited in scope by the specific embodiments, including but not limited to the deposited microorganism embodiments, herein disclosed since these embodiments are intended as illustrations of several aspects of the invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

We claim:

1. A non-transgenic herbicide resistant plant that expresses a mutant EPSPS gene product wherein the mutant EPSPS gene product comprises a Thr to Ile substitution at position $Thr_{178}$ in *Arabidopsis* (SEQ ID NO:2) or at an analogous amino acid residue in an EPSPS paralog, and a Pro to Leu at position $Pro_{182}$ in *Arabidopsis* (SEQ ID NO:2) or at an analogous amino acid residue in an EPSPS paralog, wherein the plant is selected from the group consisting of rice, soybean, flax, canola, sugar beet, wheat, and potato and the herbicide is a phosphonomethylglycine herbicide.

2. The plant according to claim 1 in which the member of the phosphonomethylglycine family is glyphosate.

3. The non-transgenic herbicide resistant plant of claim 1, wherein said plant is potato.

4. The non-transgenic herbicide resistant plant of claim 1, wherein said plant is wheat.

5. The non-transgenic herbicide resistant plant of claim 1, wherein said plant is sugarbeet.

6. A non-transgenic herbicide resistant plant cell that expresses a mutant EPSPS gene product wherein the mutant EPSPS gene product comprises a Thr to Ile substitution at position $Thr_{178}$ in *Arabidopsis* (SEQ ID NO:2) or at an analogous amino acid residue in an EPSPS paralog, and a Pro to Leu at position Pro 182 in *Arabidopsis* (SEQ ID NO:2) or at an analogous amino acid residue in an EPSPS paralog, wherein the plant cell is selected from the group consisting of a rice cell, a soybean cell, a flax cell, a canola cell, a sugarbeet cell, a wheat cell, and a potato cell and the herbicide is a phosphonomethylglycine herbicide.

7. The plant according to claim 6 in which the member of the phosphonomethylglycine family is glyphosate.

8. The non-transgenic herbicide resistant plant cell of claim 6, wherein said plant cell is a potato cell.

9. The non-transgenic herbicide resistant plant of claim 6, wherein said plant cell is a wheat cell.

10. The non-transgenic herbicide resistant plant of claim 6, wherein said plant cell is a sugarbeet cell.

* * * * *

SEQUENCE LISTING

<160> NUMBER OF SEQ ID NOS: 44

<210> SEQ ID NO 1
<211> LENGTH: 2763
<212> TYPE: DNA

<213> ORGANISM: Arabidopsis thaliana

<400> SEQUENCE: 1

| | | | | | |
|---|---|---|---|---|---|
| cccttcatgt | cttttgtaga | aaccccatta | tctttcttag | ggcccaattg | aaaacccaca | 60 |
| ttttctttca | cctaacccac | caaagccttg | cacatgttga | cgtgaacacc | aaactaacac | 120 |
| gtgtcatact | gccagtggtt | atgataaatg | ctcataccat | accagagtca | tagagttttt | 180 |
| ggttggtgaa | agatttgacg | gatgccttct | tctcatttct | caccaactcc | ctccaaaccc | 240 |
| aacaaaatgt | ttatattagc | aaagccgcca | aagtgtaaac | gaaagtttat | aaatttcatt | 300 |
| tctgtgatct | tacgtaattg | gaggaagatc | aaaattttca | atccccattc | ttcgattgct | 360 |
| tcaattgaag | tttctccgat | ggcgcaagtt | agcagaatct | gcaatggtgt | gcagaaccca | 420 |
| tctcttatct | ccaatctctc | gaaatccagt | caacgcaaat | ctcccttatc | ggtttctctg | 480 |
| aagacgcagc | agcatccacg | agcttatccg | atttcgtcgt | cgtggggatt | gaagaagagt | 540 |
| gggatgacgt | taattggctc | tgagcttcgt | cctcttaagg | tcatgtcttc | tgtttccacg | 600 |
| gcggagaaag | cgtcggagat | tgtacttcaa | cccattagag | aaatctccgg | tcttattaag | 660 |
| cttcctggct | ccaagtctct | atcaaatcgg | atcctgcttc | tcgctgctct | gtctgaggta | 720 |
| tatatcactt | cgtttcgtcc | ttctctgtaa | tctgaactta | gattataaag | attgatactt | 780 |
| taccattttg | ctgtggtttt | atagggaaca | actgtagtgg | acaacttgtt | gaatagcgat | 840 |
| gacatcaatt | acatgcttga | tgcgttgaag | agattgggac | ttaatgtgga | aactgacagt | 900 |
| gaaaataatc | gtgctgtagt | tgaaggatgt | ggcgggatat | tcccagcttc | catagattca | 960 |
| aagagtgata | tcgaacttta | cctcggtaat | gcaggaacag | caatgcgtcc | acttaccgct | 1020 |
| gcggtcactg | ctgcaggtgg | aaacgcaagg | tagattgaag | gagttgatgc | ttcttggtat | 1080 |
| ttgatgttta | aggaatggag | cttttgttga | tgctttatga | tccatttatt | ccagttatgt | 1140 |
| gcttgatggg | gtgcctcgta | tgagagaaag | acctataggg | gatttggttg | ttggtcttaa | 1200 |
| gcagcttggt | gctgatgttg | aatgtactct | tggaactaac | tgccctcctg | ttcgtgtcaa | 1260 |
| cgctaatggt | ggccttcccg | gtggaaaggt | tagatcttgc | aaatggcatg | tgaatatgta | 1320 |
| atctcgttcc | ttactctatg | aacacttgca | gaaatgtgtg | ttcatcatag | ccttagcttg | 1380 |
| acaagatttc | agttttttaat | ctactctcaa | cggatggatc | ctaaaataga | atcggatttg | 1440 |
| gtgattggtt | ttcgttctcg | attaccgttt | tcgttgtatg | atttcttgat | taacaattag | 1500 |
| gagacatgtt | atgcatttgc | aggtgaagct | ttctggatca | attagtagtc | agtacttgac | 1560 |
| tgctctgctc | atgtctgctc | ccttagctct | tggagacgtc | gagattgaga | ttgtcgataa | 1620 |
| attaatttct | gttccatatg | ttgaaatgac | attgaagttg | atggaacgtt | tcggggttag | 1680 |
| tgtcgagcat | agtgatagct | gggatcgttt | ctttgtcaag | ggcgggcaaa | atacaagta | 1740 |
| ggagttattc | ttttcttcct | tttctgaaat | cacatcccctt | agcttgacaa | tataatgact | 1800 |
| aaaaggtgaa | tgattcaggt | ctccgggtaa | tgcgtatgta | aaggtgatg | cttcagtgc | 1860 |
| atgttatttc | ttggctggtg | ctgccattac | cggtgaaact | gtcacagtcg | aaggttgtgg | 1920 |
| aactaccagc | ttgcaggtaa | tatttgtaca | ctgaatcatc | gacgaggctg | ttaagtttat | 1980 |
| agtgaaattc | gtctaggtca | aagtttcatc | ttttgacaag | ttgtatataa | catattcgca | 2040 |
| agattctaag | ctcaattttt | gtgatgaatc | tctagggaga | tgtaaaattc | gccgaggtcc | 2100 |
| ttgagaaaat | gggatgtaaa | gtgtcctgga | cagagaacag | tgtgactgtg | acaggaccac | 2160 |
| ctagagatgc | ttttgaaatg | agacacttgc | gggcttatga | tgtcaacatg | aacaaaatgc | 2220 |
| ctgatgtagc | catgacccctt | gccgtcgttg | ctctctttgc | tgacggtcca | accaccatta | 2280 |

```
gagatggtaa gtaaaaagct ctctcttata attaaggttt ctcaatattc atgatcactt    2340
aattctgttt ggttaatata gtggctagct ggagagtaaa ggagacagaa aggatgattg    2400
ccatttgcac agagcttaga aaagtaagag attcttatct ctctctttct gtctcttgac    2460
agtgctcatt ctaagtaatt agctcataaa tttgtgtgtt tgtgttcagc tgggagctac    2520
agtggaagaa ggttcagatt attgtgtgat aactccgccc aaaaaggtga aaacggcaga    2580
gattgataca tatgatgatc atagaatggc aatggcattc tctcttgcag cttgtgctga    2640
tgttccaatc accatcaacg actctggttg caccaggaaa accttccccg actacttcca    2700
agtacttgaa agaatcacaa agcactaaac aataaactct gttttttctt ctgatccaag    2760
ctt                                                                  2763
```

<210> SEQ ID NO 2
<211> LENGTH: 520
<212> TYPE: PRT
<213> ORGANISM: Arabidopsis thaliana

<400> SEQUENCE: 2

```
Met Ala Gln Val Ser Arg Ile Cys Asn Gly Val Gln Asn Pro Ser Leu
1               5                   10                  15

Ile Ser Asn Leu Ser Lys Ser Ser Gln Arg Lys Ser Pro Leu Ser Val
            20                  25                  30

Ser Leu Lys Thr Gln Gln His Pro Arg Ala Tyr Pro Ile Ser Ser Ser
        35                  40                  45

Trp Gly Leu Lys Lys Ser Gly Met Thr Leu Ile Gly Ser Glu Leu Arg
    50                  55                  60

Pro Leu Lys Val Met Ser Ser Val Ser Thr Ala Glu Lys Ala Ser Glu
65                  70                  75                  80

Ile Val Leu Gln Pro Ile Arg Glu Ile Ser Gly Leu Ile Lys Leu Pro
                85                  90                  95

Gly Ser Lys Ser Leu Ser Asn Arg Ile Leu Leu Leu Ala Ala Leu Ser
            100                 105                 110

Glu Gly Thr Thr Val Val Asp Asn Leu Leu Asn Ser Asp Asp Ile Asn
        115                 120                 125

Tyr Met Leu Asp Ala Leu Lys Arg Leu Gly Leu Asn Val Glu Thr Asp
    130                 135                 140

Ser Glu Asn Asn Arg Ala Val Val Glu Gly Cys Gly Gly Ile Phe Pro
145                 150                 155                 160

Ala Ser Ile Asp Ser Lys Ser Asp Ile Glu Leu Tyr Leu Gly Asn Ala
                165                 170                 175

Gly Thr Ala Met Arg Pro Leu Thr Ala Ala Val Thr Ala Ala Gly Gly
            180                 185                 190

Asn Ala Ser Tyr Val Leu Asp Gly Val Pro Arg Met Arg Glu Arg Pro
        195                 200                 205

Ile Gly Asp Leu Val Val Gly Leu Lys Gln Leu Gly Ala Asp Val Glu
    210                 215                 220

Cys Thr Leu Gly Thr Asn Cys Pro Pro Val Arg Val Asn Ala Asn Gly
225                 230                 235                 240

Gly Leu Pro Gly Gly Lys Val Lys Leu Ser Gly Ser Ile Ser Ser Gln
                245                 250                 255

Tyr Leu Thr Ala Leu Leu Met Ser Ala Pro Leu Ala Leu Gly Asp Val
            260                 265                 270

Glu Ile Glu Ile Val Asp Lys Leu Ile Ser Val Pro Tyr Val Glu Met
```

```
                    275                 280                 285
Thr Leu Lys Leu Met Glu Arg Phe Gly Val Ser Val Glu His Ser Asp
    290                 295                 300

Ser Trp Asp Arg Phe Phe Val Lys Gly Gly Gln Lys Tyr Lys Ser Pro
305                 310                 315                 320

Gly Asn Ala Tyr Val Glu Gly Asp Ala Ser Ala Cys Tyr Phe Leu
                325                 330                 335

Ala Gly Ala Ala Ile Thr Gly Glu Thr Val Thr Val Gly Cys Gly
            340                 345                 350

Thr Thr Ser Leu Gln Gly Asp Val Lys Phe Ala Glu Val Leu Glu Lys
        355                 360                 365

Met Gly Cys Lys Val Ser Trp Thr Glu Asn Ser Val Thr Val Thr Gly
    370                 375                 380

Pro Pro Arg Asp Ala Phe Gly Met Arg His Leu Arg Ala Ile Asp Val
385                 390                 395                 400

Asn Met Asn Lys Met Pro Asp Val Ala Met Thr Leu Ala Val Val Ala
                405                 410                 415

Leu Phe Ala Asp Gly Pro Thr Thr Ile Arg Asp Val Ala Ser Trp Arg
            420                 425                 430

Val Lys Glu Thr Glu Arg Met Ile Ala Ile Cys Thr Glu Leu Arg Lys
        435                 440                 445

Leu Gly Ala Thr Val Glu Glu Gly Ser Asp Tyr Cys Val Ile Thr Pro
    450                 455                 460

Pro Lys Lys Val Lys Thr Ala Glu Ile Asp Thr Tyr Asp Asp His Arg
465                 470                 475                 480

Met Ala Met Ala Phe Ser Leu Ala Ala Cys Ala Asp Val Pro Ile Thr
                485                 490                 495

Ile Asn Asp Ser Gly Cys Thr Arg Lys Thr Phe Pro Asp Tyr Phe Gln
            500                 505                 510

Val Leu Glu Arg Ile Thr Lys His
        515                 520

<210> SEQ ID NO 3
<211> LENGTH: 33
<212> TYPE: DNA
<213> ORGANISM: Arabidopsis thaliana
<220> FEATURE:
<221> NAME/KEY: CDS
<222> LOCATION: (1)...(33)

<400> SEQUENCE: 3 ctc ggt aat gca gca aca gca atg cgt cca ctt                          33
Leu Gly Asn Ala Ala Thr Ala Met Arg Pro Leu
 1               5                  10

<210> SEQ ID NO 4
<211> LENGTH: 11
<212> TYPE: PRT
<213> ORGANISM: Arabidopsis thaliana

<400> SEQUENCE: 4

Leu Gly Asn Ala Ala Thr Ala Met Arg Pro Leu
 1               5                  10

<210> SEQ ID NO 5
<211> LENGTH: 33
<212> TYPE: DNA
<213> ORGANISM: Arabidopsis thaliana
<220> FEATURE:
```

```
<221> NAME/KEY: CDS
<222> LOCATION: (1)...(33)

<400> SEQUENCE: 5 ctc ggt aat gca gga ata gca atg cgt cca ctt                    33
Leu Gly Asn Ala Gly Ile Ala Met Arg Pro Leu
 1               5                  10

<210> SEQ ID NO 6
<211> LENGTH: 11
<212> TYPE: PRT
<213> ORGANISM: Arabidopsis thaliana

<400> SEQUENCE: 6

Leu Gly Asn Ala Gly Ile Ala Met Arg Pro Leu
 1               5                  10

<210> SEQ ID NO 7
<211> LENGTH: 33
<212> TYPE: DNA
<213> ORGANISM: Arabidopsis thaliana
<220> FEATURE:
<221> NAME/KEY: CDS
<222> LOCATION: (1)...(33)

<400> SEQUENCE: 7 ctc ggt aat gca gca ata gca atg cgt cca ctt                    33
Leu Gly Asn Ala Ala Ile Ala Met Arg Pro Leu
 1               5                  10

<210> SEQ ID NO 8
<211> LENGTH: 11
<212> TYPE: PRT
<213> ORGANISM: Arabidopsis thaliana

<400> SEQUENCE: 8

Leu Gly Asn Ala Ala Ile Ala Met Arg Pro Leu
 1               5                  10

<210> SEQ ID NO 9
<211> LENGTH: 33
<212> TYPE: DNA
<213> ORGANISM: Arabidopsis thaliana
<220> FEATURE:
<221> NAME/KEY: CDS
<222> LOCATION: (1)...(33)

<400> SEQUENCE: 9 ctc ggt aat gca gga ata gca atg cgt tca ctt                    33
Leu Gly Asn Ala Gly Ile Ala Met Arg Ser Leu
 1               5                  10

<210> SEQ ID NO 10
<211> LENGTH: 11
<212> TYPE: PRT
<213> ORGANISM: Arabidopsis thaliana

<400> SEQUENCE: 10

Leu Gly Asn Ala Gly Ile Ala Met Arg Ser Leu
 1               5                  10

<210> SEQ ID NO 11
<211> LENGTH: 33
<212> TYPE: DNA
<213> ORGANISM: Arabidopsis thaliana
<220> FEATURE:
<221> NAME/KEY: CDS
```

-continued

```
<222> LOCATION: (1)...(33)

<400> SEQUENCE: 11 ctc ggt aat gca gca aca gca atg cgt tca ctt                    33
Leu Gly Asn Ala Ala Thr Ala Met Arg Ser Leu
 1               5                  10

<210> SEQ ID NO 12
<211> LENGTH: 11
<212> TYPE: PRT
<213> ORGANISM: Arabidopsis thaliana

<400> SEQUENCE: 12

Leu Gly Asn Ala Ala Thr Ala Met Arg Ser Leu
 1               5                  10

<210> SEQ ID NO 13
<211> LENGTH: 33
<212> TYPE: DNA
<213> ORGANISM: Arabidopsis thaliana
<220> FEATURE:
<221> NAME/KEY: CDS
<222> LOCATION: (1)...(33)

<400> SEQUENCE: 13 ctc ggt aat gca gca ata gca atg cgt tca ctt                    33
Leu Gly Asn Ala Ala Ile Ala Met Arg Ser Leu
 1               5                  10

<210> SEQ ID NO 14
<211> LENGTH: 11
<212> TYPE: PRT
<213> ORGANISM: Arabidopsis thaliana

<400> SEQUENCE: 14

Leu Gly Asn Ala Ala Ile Ala Met Arg Ser Leu
 1               5                  10

<210> SEQ ID NO 15
<211> LENGTH: 33
<212> TYPE: DNA
<213> ORGANISM: Arabidopsis thaliana
<220> FEATURE:
<221> NAME/KEY: CDS
<222> LOCATION: (1)...(33)

<400> SEQUENCE: 15 ctc ggt aat gca gga gta gca atg cgt tca ctt                    33
Leu Gly Asn Ala Gly Val Ala Met Arg Ser Leu
 1               5                  10

<210> SEQ ID NO 16
<211> LENGTH: 11
<212> TYPE: PRT
<213> ORGANISM: Arabidopsis thaliana

<400> SEQUENCE: 16

Leu Gly Asn Ala Gly Val Ala Met Arg Ser Leu
 1               5                  10

<210> SEQ ID NO 17
<211> LENGTH: 33
<212> TYPE: DNA
<213> ORGANISM: Arabidopsis thaliana
<220> FEATURE:
<221> NAME/KEY: CDS
<222> LOCATION: (1)...(33)
```

```
<400> SEQUENCE: 17 ctc ggt aat gca gga tta gca atg cgt tca ctt            33
Leu Gly Asn Ala Gly Leu Ala Met Arg Ser Leu
  1               5                  10

<210> SEQ ID NO 18
<211> LENGTH: 11
<212> TYPE: PRT
<213> ORGANISM: Arabidopsis thaliana

<400> SEQUENCE: 18

Leu Gly Asn Ala Gly Leu Ala Met Arg Ser Leu
  1               5                  10

<210> SEQ ID NO 19
<211> LENGTH: 33
<212> TYPE: DNA
<213> ORGANISM: Arabidopsis thaliana
<220> FEATURE:
<221> NAME/KEY: CDS
<222> LOCATION: (1)...(33)

<400> SEQUENCE: 19 ctc ggt aat gca gca gta gca atg cgt cca ctt            33
Leu Gly Asn Ala Ala Val Ala Met Arg Pro Leu
  1               5                  10

<210> SEQ ID NO 20
<211> LENGTH: 11
<212> TYPE: PRT
<213> ORGANISM: Arabidopsis thaliana

<400> SEQUENCE: 20

Leu Gly Asn Ala Ala Val Ala Met Arg Pro Leu
  1               5                  10

<210> SEQ ID NO 21
<211> LENGTH: 33
<212> TYPE: DNA
<213> ORGANISM: Arabidopsis thaliana
<220> FEATURE:
<221> NAME/KEY: CDS
<222> LOCATION: (1)...(33)

<400> SEQUENCE: 21 ctc ggt aat gca gca tta gca atg cgt cca ctt            33
Leu Gly Asn Ala Ala Leu Ala Met Arg Pro Leu
  1               5                  10

<210> SEQ ID NO 22
<211> LENGTH: 11
<212> TYPE: PRT
<213> ORGANISM: Arabidopsis thaliana

<400> SEQUENCE: 22

Leu Gly Asn Ala Ala Leu Ala Met Arg Pro Leu
  1               5                  10

<210> SEQ ID NO 23
<211> LENGTH: 3831
<212> TYPE: DNA
<213> ORGANISM: Brassisca napus
<220> FEATURE:
<221> NAME/KEY: modified_base
<222> LOCATION: 1...3831
<223> OTHER INFORMATION: n=a, c, g, or t
```

<400> SEQUENCE: 23

```
agatcttaaa ggctctttc cagtctcacc taccaaaact ataagaaaat ccacttgctg      60
tctgaaatag ccgacgtgga taaagtactt aagacgtggc acattattat tggctactag    120
aaaaaaaact catacaccat cgtaggagtt ggggttggtg aagaatttga tgggtgcctc    180
tccccccccc actcaccaaa ctcatgttct ttgtaaagcc gtcactacaa caacaaagga    240
gacgacagtt ctatagaaaa gctttcaaat tcaatcaatg cgcaatcta gcagaatctg     300
ccatggcgtg cagaacccat gtgttatcat ctccaatctc tccaaatcca accaaaacaa    360
atcacctttc tccgtctcct tgaagacgca tcagcctcga gcttcttcgt ggggattgaa    420
gaagagtgga acgatgctaa acggttctgt aattcgcccg gttaaggtaa cagcttctgt    480
ttccacgtcc gagaaagctt cagagattgt gcttcaacca atcagagaaa tctcgggtct    540
cattaagcta cccggatcca atctctctc caatcggatc ctccttcttg ccgctctatc     600
tgaggtacat atacttgctt agtgttaggc ctttgctgtg agattttggg aactatagac    660
aatttagtaa gaatttatat ataatttttt taaaaaaaat cagaagccta tatatattta    720
aattttccca aatttttggg aggttatagg cttatgttac accattctag tctgcatctt    780
tcggtttgag actgaagaat tttattttt aaaaaattat tatagggaac tactgtagtg     840
gacaacttgt tgaacagtga tgacatcaac tacatgcttg atgcgttgaa gaagctgggg    900
cttaacgtgg aacgtgacag tgtaaacaac cgtgcggttg ttgaaggatg cggtggaata    960
ttcccagctt ccttagattc caagagtgat attgagttgt accttgggaa tgcaggaaca   1020
gccatgcgtc cactcaccgc tgcagttaca gctgcaggtg gcaacgcgag gtaaggttaa   1080
cgagtttttt gttattgtca agaaattgat cttgtgtttg atgcttttag tttggttgt    1140
tttctagtta tgtacttgat ggggtgccta gaatgaggga aagacctata ggagatttgg   1200
ttgttggtct taagcagctt ggtgctgatg ttgagtgtac tcttggcact aactgtcctc   1260
ctgttcgtgt caatgctaat ggtggccttc ccggtggaaa ggtgatcttc acatttactc   1320
tatgaattgt ttgcagcagt cttgttcat cacagccttt gcttcacatt atttcatctt    1380
ttagtttgtt gttatattac ttgatggatc tttaaaagg aattgggtct ggtgtgaaag    1440
tgattagcaa tctttctcga ttccttgcag ggccgtgggc attactaagt gaaacattag   1500
cctattaacc cccaaaattt tgaaaaaaa tttagtatat ggcccaaaa tagttttta      1560
aaaaattaga aaactttta ataaatcgtc tacagtcccn naaatcttag agccggccct    1620
gcttgtatgg tttctcgatt gatatattag actatgtttt gaattttcag gtgaagcttt   1680
ctggatcgat cagtagtcag tacttgactg ccctcctcat ggcagctcct ttagctcttg   1740
gagacgtgga gattgagatc attgataaac tgatatctgt tccatatgtt gaatgacat    1800
tgaagttgat ggagcgtttt ggtgttagtg ccgagcatag tgatagctgg gatcgtttct   1860
ttgtcaaggg cggtcagaaa tacaagtaat gagttctttt aagttgagag ttagattgaa   1920
gaatgaatga ctgattaacc aaatggcaaa actgattcag gtcgcctggt aatgcttatg   1980
tagaaggtga tgcttctagt gctagctatt tcttggctgg tgctgccatt actggtgaaa   2040
ctgttactgt cgaaggttgt ggaacaacta gcctccaggt agtttatcca ctctgaatca   2100
tcaaatatta ttctccctcc gttttatgtt aagtgtcatt agcttttaaa ttttgtttca   2160
ttaaaagtgt cattttacat tttcaatgca tatattaaat aaattttcca gttttttacta  2220
attcattaat tagcaaaatc aaacaaaaat tatattaaat aatgtaaaat tcgtaatttg   2280
```

```
tgtgcaaata ccttaaacct tatgaaacgg aaaccttatg aaacagaggg agtactaatt    2340
ttataataaa atttgattag ttcaaagttg tgtataacat gttttgtaag aatctaagct    2400
cattctcttt ttattttttg tgatgaatcc aaagggagat gtgaaattcg cagaggttct    2460
tgagaaaatg ggatgtaaag tgtcatggac agagaacagt gtgactgtga ctggaccatc    2520
aagagatgct tttggaatga ggcacttgcg tgctgttgat gtcaacatga acaaaatgcc    2580
tgatgtagcc atgactctag ccgttgttgc tctctttgcc gatggtccaa ccaccatcag    2640
agatggtaaa gcaaaaccct ctctttgaat cagcgtgttt taaaagattc atggttgctt    2700
aaactctatt tggtcaatgt agtggctagc tggagagtta aggagacaga gaggatgatt    2760
gccatttgca cagagcttag aaaggtaagt ttccttttct ctcatgctct ctcattcgaa    2820
gttaatcgtt gcataacttt ttgcggtttt tttttttgcg ttcagcttgg agctacagtg    2880
gaagaaggtt cagattattg tgtgataact ccaccagcaa aggtgaaacc ggcggagatt    2940
gatacgtatg atgatcatag aatggcgatg gcgttctcgc ttgcagcttg tgctgatgtt    3000
ccagtcacca tcaaggatcc tggctgcacc aggaagactt ccctgactac ttccaagtc     3060 cttgaaagta tcacaaagca ttaaaagacc cttcctctg atccaaatgt gagaatctgt     3120
tgctttctct ttgttgccac tgtaacattt attagaagaa caaagtgtgt gtgttaagag    3180
tgtgtttgct tgtaatgaac tgagtgagat gcaatcgttg aatcagtttt gggccttaat    3240
aaagggttta ggaagctgca gcgagatgat tgttttttgat cgatcatctt tgaaaatgtg    3300
tttgtttgag taattttttct agggttgagt tgattacact aagaaacact ttttgatttt    3360 ctattcacc tatagacact tcttacatgt gacacacttt gttgttggca agcaacagat      3420
tgtggacaat tttgccttta atggaaagaa cacagttgtg gatgggtgat tgtggacga     3480 ttccatgtgt ggttagggtg atttgtggac ggatgatgtg tagatgagtg atgagtaatg    3540
tgtgaatatg tgatgttaat gtgtttatag tagataagtg gacaaactct ctgttttgat    3600
tccataaaac tatacaacaa tacgtggaca tggactcatg ttactaaaat tataccgtaa    3660
aacgtggaca cggactctgt atctccaata caaacacttg gcttcttcag ctcaattgat    3720
aaattatctg cagttaaact tcaatcaaga tgagaaagag atgatattgt gaatatgagc    3780
ggagagagaa atcgaagaag cgtttaccctt ttgtcggaga gtaatagatc t             3831
```

```
<210> SEQ ID NO 24
<211> LENGTH: 1944
<212> TYPE: DNA
<213> ORGANISM: Petunia hybrida

<400> SEQUENCE: 24
```

```
gaattccctc aatctttact ttcaagaatg gcacaaatta caacatggc tcaagggata      60 caaacccctta atcccaattc caatttccat aaaccccaag ttcctaaatc ttcaagtttt    120 cttgttttg gatctaaaaa actgaaaaat tcagcaaatt ctatgttggt tttgaaaaaa     180
gattcaattt ttatgcaaaa gttttgttcc tttaggattt cagcatcagt ggctacagca    240
cagaagcctt ctgagatagt gttgcaaccc attaaagaga tttcaggcac tgttaaattg    300
cctggctcta atcattatc taatagaatt ctccttcttg ctgccttatc tgaaggaaca     360
actgtggttg acaatttact aagtagtgat gatattcatt acatgcttgg tgccttgaaa    420
acacttggac tgcatgtaga agaagatagt gcaaaccaac gagctgttgt tgaaggttgt    480
ggtgggcttt tccctgttgg taagagtcc aaggaagaaa ttcaactgtt ccttggaaat     540
gcaggaacag caatgcggcc actaacagca gcagttactg tagctggtgg aaattcaagg    600
```

```
tatgtacttg atggagttcc tcgaatgaga gagagaccaa ttagtgattt ggttgatggt      660
cttaaacagc ttggtgcaga ggttgattgt ttccttggta cgaaatgtcc tcctgttcga      720
attgtcagca agggaggtct tcctggaggg aaggtcaagc tctctggatc cattagcagc      780
caatacttga ctgctctgct tatggctgct ccactggctt taggagatgt ggagattgaa      840
atcattgaca aactaattag tgtaccttat gtcgagatga cattgaagtt gatggagcga      900 tttggtatttt ctgtggagca cagtagtagc tgggacaggt tctttgtccg aggaggtcag      960
aaatacaagt ctcctggaaa agcttttgtc gaaggtgatg cttcaagtgc tagctacttc     1020
ttggctggtg cagcagtcac aggtggaact atcactgttg aaggttgtgg gacaaacagt     1080 ttacagggggg atgtcaaatt tgctgaggta cttgaaaaaa tgggagctga agttacgtgg     1140
acagagaaca gtgtcacagt caaaggacct ccaaggagtt cttctgggag gaagcatttg     1200
cgtgccattg atgtgaacat gaataaaatg cctgatgttg ccatgacact tgctgttgtt     1260
gcactttatg ctgatggtcc cacagctata agagatgttg ctagctggag agtcaaggaa     1320
actgagcgca tgatcgccat atgcacagaa cttaggaagt taggagcaac cgttgaagaa     1380
ggaccagact actgcataat cacccccaccg gagaaactaa atgtgaccga tattgataca     1440
tacgatgatc acaggatggc catggctttt tctcttgctg cttgtgcaga tgttcccgtc     1500
accatcaatg accctggctg cacgcggaaa accttcccta actactttga tgtacttcag     1560
cagtactcca agcattgaac cgcttccccta tattgcagaa tgtaagtaag aatatgtgaa     1620
gagtttagtt cttgtacaag acaggctacg actgcctggt atcagaacca caatgggttc     1680
catttcagtt cagaagggca ttccaaggct tcgaactctt tacttatttg cgagtgatga     1740
aatgtatttg ttagagttga gcttcttttt gtctttaagg aatgtacact aatagagtta     1800
agaattacta gtatgggcca gtgtaaggag tactattact cttttgcttat tttattgatt     1860 gagttttgtc aaggatctgg ctttgtcaag aattactggt taatttttatt gacaatctca     1920 tgtgtctaaa tgaaattgtt tgat                                            1944
```

<210> SEQ ID NO 25
<211> LENGTH: 1335
<212> TYPE: DNA
<213> ORGANISM: Zea mays

<400> SEQUENCE: 25

```
gcgggtgccg aggagatcgt gctgcagccc atcaaggaga tctccggcac cgtcaagctg       60
ccggggtcca agtcgctttc caaccggatc ctcctactcg ccgccctgtc cgaggggaca      120
acagtggttg ataacctgct gaacagtgag gatgtccact acatgctcgg ggccttgagg      180
actcttggtc tctctgtcga agcggacaaa gctgccaaaa gagctgtagt tgttggctgt      240
ggtggaaagt tcccagttga ggatgctaaa gaggaagtgc agctcttctt ggggaatgct      300
ggaactgcaa tgcggccatt gacagcagct gttactgctg ctggtggaaa tgcaacttac      360
gtgcttgatg gagtaccaag aatgagggag agacccattg gcgacttggt tgtcggattg      420
aagcagcttg gtgcagatgt tgattgtttc cttggcactg actgcccacc tgttcgtgtc      480
aatggaatcg gagggctacc tggtggcaag gtcaagctgt ctggctccat cagcagtcag      540
tacttgagtg ccttgctgat ggctgctcct ttggctcttg gggatgtgga gattgaaatc      600
attgataaat taatctccat tccgtacgtc gaaatgacat tgagattgat ggagcgtttt      660
ggtgtgaaag cagagcattc tgatagctgg gacagattct acattaaggg aggtcaaaaa      720
```

```
tacaagtccc ctaaaaatgc ctatgttgaa ggtgatgcct caagcgcaag ctatttcttg    780
gctggtgctg caattactgg agggactgtg actgtggaag gttgtggcac caccagtttg    840
cagggtgatg tgaagtttgc tgaggtactg agatgatgg gagcgaaggt tacatggacc     900
gagactagcg taactgttac tggcccaccg cgggagccat ttgggaggaa acacctcaag    960
gcgattgatg tcaacatgaa caagatgcct gatgtcgcca tgactcttgc tgtggttgcc   1020
ctctttgccg atggcccgac agccatcaga gacgtggctt cctggagagt aaaggagacc   1080
gagaggatgg ttgcgatccg gacggagcta accaagctgg gagcatctgt tgaggaaggg   1140
ccggactact gcatcatcac gccgccggag aagctgaacg tgacggcgat cgacacgtac   1200
gacgaccaca ggatggccat ggccttctcc cttgccgcct gtgccgaggt ccccgtcacc   1260
atccgggacc ctgggtgcac ccggaagacc ttccccgact acttcgatgt gctgagcact   1320
ttcgtcaaga attaa                                                    1335
```

<210> SEQ ID NO 26
<211> LENGTH: 516
<212> TYPE: PRT
<213> ORGANISM: Brassisca napus

<400> SEQUENCE: 26

```
Met Ala Gln Ser Ser Arg Ile Cys His Gly Val Gln Asn Pro Cys Val
1               5                   10                  15

Ile Ile Ser Asn Leu Ser Lys Ser Gln Asn Lys Ser Pro Phe Ser
            20                  25                  30

Val Ser Leu Lys Thr His Gln Pro Arg Ala Ser Ser Trp Gly Leu Lys
        35                  40                  45

Lys Ser Gly Thr Met Leu Asn Gly Ser Val Ile Arg Pro Val Lys Val
    50                  55                  60

Thr Ala Ser Val Ser Thr Ser Glu Lys Ala Ser Glu Ile Val Leu Gln
65                  70                  75                  80

Pro Ile Arg Glu Ile Ser Gly Leu Ile Lys Leu Pro Gly Ser Lys Ser
                85                  90                  95

Leu Ser Asn Arg Ile Leu Leu Leu Ala Ala Leu Ser Glu Gly Thr Thr
            100                 105                 110

Val Val Asp Asn Leu Leu Asn Ser Asp Asp Ile Asn Tyr Met Leu Asp
        115                 120                 125

Ala Leu Lys Lys Leu Gly Leu Asn Val Glu Arg Asp Ser Val Asn Asn
    130                 135                 140

Arg Ala Val Val Glu Gly Cys Gly Gly Ile Phe Pro Ala Ser Leu Asp
145                 150                 155                 160

Ser Lys Ser Asp Ile Glu Leu Tyr Leu Gly Asn Ala Gly Thr Ala Met
                165                 170                 175

Arg Pro Leu Thr Ala Ala Val Thr Ala Ala Gly Gly Asn Ala Ser Tyr
            180                 185                 190

Val Leu Asp Gly Val Pro Arg Met Arg Glu Arg Pro Ile Gly Asp Leu
        195                 200                 205

Val Val Gly Leu Lys Gln Leu Gly Ala Asp Val Glu Cys Thr Leu Gly
    210                 215                 220

Thr Asn Cys Pro Pro Val Arg Val Asn Ala Asn Gly Gly Leu Pro Gly
225                 230                 235                 240

Gly Lys Val Lys Leu Ser Gly Ser Ile Ser Ser Gln Tyr Leu Thr Ala
                245                 250                 255

Leu Leu Met Ala Ala Pro Leu Ala Leu Gly Asp Val Glu Ile Glu Ile
```

```
            260                 265                 270
Ile Asp Lys Leu Ile Ser Val Pro Tyr Val Glu Met Thr Leu Lys Leu
            275                 280                 285

Met Glu Arg Phe Gly Val Ser Ala Glu His Ser Asp Ser Trp Asp Arg
        290                 295                 300

Phe Val Lys Gly Gly Gln Lys Tyr Lys Ser Pro Gly Asn Ala Tyr
305                 310                 315                 320

Val Glu Gly Asp Ala Ser Ser Ala Ser Tyr Phe Leu Ala Gly Ala Ala
                325                 330                 335

Ile Thr Gly Glu Thr Val Thr Val Glu Gly Cys Gly Thr Thr Ser Leu
            340                 345                 350

Gln Gly Asp Val Lys Phe Ala Glu Val Leu Glu Lys Met Gly Cys Lys
        355                 360                 365

Val Ser Trp Thr Glu Asn Ser Val Thr Val Thr Gly Pro Ser Arg Asp
    370                 375                 380

Ala Phe Gly Met Arg His Leu Arg Ala Val Asp Val Asn Met Asn Lys
385                 390                 395                 400

Met Pro Asp Val Ala Met Thr Leu Ala Val Ala Leu Phe Ala Asp
                405                 410                 415

Gly Pro Thr Thr Ile Arg Asp Val Ala Ser Trp Arg Val Lys Glu Thr
                420                 425                 430

Glu Arg Met Ile Ala Ile Cys Thr Glu Leu Arg Lys Leu Gly Ala Thr
            435                 440                 445

Val Glu Glu Gly Ser Asp Tyr Cys Val Ile Thr Pro Pro Ala Lys Val
    450                 455                 460

Lys Pro Ala Glu Ile Asp Thr Tyr Asp Asp His Arg Met Ala Met Ala
465                 470                 475                 480

Phe Ser Leu Ala Ala Cys Ala Asp Val Pro Val Thr Ile Lys Asp Pro
                485                 490                 495

Gly Cys Thr Arg Lys Thr Phe Pro Asp Tyr Phe Gln Val Leu Glu Ser
                500                 505                 510

Ile Thr Lys His
        515

<210> SEQ ID NO 27
<211> LENGTH: 516
<212> TYPE: PRT
<213> ORGANISM: Petunia hybrida

<400> SEQUENCE: 27

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Lys Phe Cys Ser Phe Arg Ile
    50                  55                  60

Ser Ala Ser Val Ala Thr Ala Gln Lys Pro Ser Glu Ile Val Leu Gln
65                  70                  75                  80

Pro Ile Lys Glu Ile Ser Gly Thr Val Lys Leu Pro Gly Ser Lys Ser
                85                  90                  95

Leu Ser Asn Arg Ile Leu Leu Leu Ala Ala Leu Ser Glu Gly Thr Thr
            100                 105                 110
```

```
Val Val Asp Asn Leu Leu Ser Ser Asp Asp Ile His Tyr Met Leu Gly
            115                 120                 125
Ala Leu Lys Thr Leu Gly Leu His Val Glu Glu Asp Ser Ala Asn Gln
130                 135                 140
Arg Ala Val Val Glu Gly Cys Gly Gly Leu Phe Pro Val Gly Lys Glu
145                 150                 155                 160
Ser Lys Glu Glu Ile Gln Leu Phe Leu Gly Asn Ala Gly Thr Ala Met
                165                 170                 175
Arg Pro Leu Thr Ala Ala Val Thr Val Ala Gly Gly Asn Ser Arg Tyr
            180                 185                 190
Val Leu Asp Gly Val Pro Arg Met Arg Glu Arg Pro Ile Ser Asp Leu
    195                 200                 205
Val Asp Gly Leu Lys Gln Leu Gly Ala Glu Val Asp Cys Phe Leu Gly
210                 215                 220
Thr Lys Cys Pro Pro Val Arg Ile Val Ser Lys Gly Gly Leu Pro Gly
225                 230                 235                 240
Gly Lys Val Lys Leu Ser Gly Ser Ile Ser Ser Gln Tyr Leu Thr Ala
                245                 250                 255
Leu Leu Met Ala Ala Pro Leu Ala Leu Gly Asp Val Glu Ile Glu Ile
            260                 265                 270
Ile Asp Lys Leu Ile Ser Val Pro Tyr Val Glu Met Thr Leu Lys Leu
    275                 280                 285
Met Glu Arg Phe Gly Ile Ser Val Glu His Ser Ser Ser Trp Asp Arg
290                 295                 300
Phe Phe Val Arg Gly Gly Gln Lys Tyr Lys Ser Pro Gly Lys Ala Phe
305                 310                 315                 320
Val Glu Gly Asp Ala Ser Ser Ala Ser Tyr Phe Leu Ala Gly Ala Ala
                325                 330                 335
Val Thr Gly Gly Thr Ile Thr Val Glu Gly Cys Gly Thr Asn Ser Leu
            340                 345                 350
Gln Gly Asp Val Lys Phe Ala Glu Val Leu Glu Lys Met Gly Ala Glu
    355                 360                 365
Val Thr Trp Thr Glu Asn Ser Val Thr Val Lys Gly Pro Pro Arg Ser
370                 375                 380
Ser Ser Gly Arg Lys His Leu Arg Ala Ile Asp Val Asn Met Asn Lys
385                 390                 395                 400
Met Pro Asp Val Ala Met Thr Leu Ala Val Val Ala Leu Tyr Ala Asp
                405                 410                 415
Gly Pro Thr Ala Ile Arg Asp Val Ala Ser Trp Arg Val Lys Glu Thr
            420                 425                 430
Glu Arg Met Ile Ala Ile Cys Thr Glu Leu Arg Lys Leu Gly Ala Thr
    435                 440                 445
Val Glu Glu Gly Pro Asp Tyr Cys Ile Ile Thr Pro Pro Glu Lys Leu
450                 455                 460
Asn Val Thr Asp Ile Asp Thr Tyr Asp Asp His Arg Met Ala Met Ala
465                 470                 475                 480
Phe Ser Leu Ala Ala Cys Ala Asp Val Pro Val Thr Ile Asn Asp Pro
                485                 490                 495
Gly Cys Thr Arg Lys Thr Phe Pro Asn Tyr Phe Asp Val Leu Gln Gln
            500                 505                 510
Tyr Ser Lys His
        515
```

<210> SEQ ID NO 28
<211> LENGTH: 444
<212> TYPE: PRT
<213> ORGANISM: Zea mays

<400> SEQUENCE: 28

```
Ala Gly Ala Glu Glu Ile Val Leu Gln Pro Ile Lys Glu Ile Ser Gly
1               5                   10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Val Gln Leu Phe
                85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380
```

```
Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
            405                 410                 415

Val Pro Val Thr Ile Arg Asp Pro Gly Cys Thr Arg Lys Thr Phe Pro
        420                 425                 430

Asp Tyr Phe Asp Val Leu Ser Thr Phe Val Lys Asn
        435                 440
```

```
<210> SEQ ID NO 29
<211> LENGTH: 64
<212> TYPE: DNA
<213> ORGANISM: Artificial Sequence
<220> FEATURE:
<223> OTHER INFORMATION: Mutant primer

<400> SEQUENCE: 29
cgtttccacc tgcagcagtg accgcagcgg taagtggacg cattgctgtt gctgcattac    60
cgag                                                                 64

<210> SEQ ID NO 30
<211> LENGTH: 64
<212> TYPE: DNA
<213> ORGANISM: Artificial Sequence
<220> FEATURE:
<223> OTHER INFORMATION: Mutant primer

<400> SEQUENCE: 30
cgtttccacc tgcagcagtg accgcagcgg taagtggacg cattgctatt gctgcattac    60
cgag                                                                 64

<210> SEQ ID NO 31
<211> LENGTH: 64
<212> TYPE: DNA
<213> ORGANISM: Artificial Sequence
<220> FEATURE:
<223> OTHER INFORMATION: Mutant primer

<400> SEQUENCE: 31
cgtttccacc tgcagcagtg accgcagcgg taagtgaacg cattgctatt cctgcattac    60
cgag                                                                 64

<210> SEQ ID NO 32
<211> LENGTH: 64
<212> TYPE: DNA
<213> ORGANISM: Artificial Sequence
<220> FEATURE:
<223> OTHER INFORMATION: Mutant primer

<400> SEQUENCE: 32
cgtttccacc tgcagcagtg accgcagcgg taagtgaacg cattgctgtt gctgcattac    60
cgag                                                                 64

<210> SEQ ID NO 33
<211> LENGTH: 64
<212> TYPE: DNA
<213> ORGANISM: Artificial Sequence
<220> FEATURE:
<223> OTHER INFORMATION: Mutant primer

<400> SEQUENCE: 33
cgtttccacc tgcagcagtg accgcagcgg taagtgaacg cattgctatt gctgcattac    60
```

-continued cgag                                                              64

<210> SEQ ID NO 34
<211> LENGTH: 64
<212> TYPE: DNA
<213> ORGANISM: Artificial Sequence
<220> FEATURE:
<223> OTHER INFORMATION: Mutant primer

<400> SEQUENCE: 34
cgtttccacc tgcagcagtg accgcagcgg taagtggacg cattgctgtt attgcattac    60
cgag                                                              64

<210> SEQ ID NO 35
<211> LENGTH: 64
<212> TYPE: DNA
<213> ORGANISM: Artificial Sequence
<220> FEATURE:
<223> OTHER INFORMATION: Mutant primer

<400> SEQUENCE: 35
cgtttccacc tgcagcagtg accgcagcgg taagtgaacg cattgctact cctgcattac    60
cgag                                                              64

<210> SEQ ID NO 36
<211> LENGTH: 64
<212> TYPE: DNA
<213> ORGANISM: Artificial Sequence
<220> FEATURE:
<223> OTHER INFORMATION: Mutant primer

<400> SEQUENCE: 36
cgtttccacc tgcagcagtg accgcagcgg taagtgaacg cattgctaat cctgcattac    60
cgag                                                              64

<210> SEQ ID NO 37
<211> LENGTH: 64
<212> TYPE: DNA
<213> ORGANISM: Artificial Sequence
<220> FEATURE:
<223> OTHER INFORMATION: Mutant primer

<400> SEQUENCE: 37
cgtttccacc tgcagcagtg accgcagcgg taagtggacg cattgctact gctgcattac    60
cgag                                                              64

<210> SEQ ID NO 38
<211> LENGTH: 64
<212> TYPE: DNA
<213> ORGANISM: Artificial Sequence
<220> FEATURE:
<223> OTHER INFORMATION: Mutant primer

<400> SEQUENCE: 38
cgtttccacc tgcagcagtg accgcagcgg taagtggacg cattgctaat gctgcattac    60
cgag                                                              64

<210> SEQ ID NO 39
<211> LENGTH: 5
<212> TYPE: PRT
<213> ORGANISM: Petunia hybrida

```
<400> SEQUENCE: 39

Leu Phe Leu Gly Asn
1               5

<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40
gctctagaga aagcgtcgga gattgtactt                              30

<210> SEQ ID NO 41
<211> LENGTH: 41
<212> TYPE: DNA
<213> ORGANISM: Artificial Sequence
<220> FEATURE:
<223> OTHER INFORMATION: Primer

<400> SEQUENCE: 41
gcagatctga gctcttagtg ctttgtgatt ctttcaagta c                 41

<210> SEQ ID NO 42
<211> LENGTH: 28
<212> TYPE: DNA
<213> ORGANISM: Artificial Sequence
<220> FEATURE:
<223> OTHER INFORMATION: Primer

<400> SEQUENCE: 42
gcgtctagaa aaacgagata aggtgcag                                28

<210> SEQ ID NO 43
<211> LENGTH: 38
<212> TYPE: DNA
<213> ORGANISM: Artificial Sequence
<220> FEATURE:
<223> OTHER INFORMATION: Primer

<400> SEQUENCE: 43
gcggatcctc aggatttttt cgaaagctta tttaaatg                     38

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
gaaagcgtcg gagattgtac                                         20
```